(12) United States Patent
Wiegand et al.

(10) Patent No.: US 7,306,799 B2
(45) Date of Patent: *Dec. 11, 2007

(54) USE OF VEGF INHIBITORS FOR TREATMENT OF EYE DISORDERS

(75) Inventors: Stanley J. Wiegand, Croton on Hudson, NY (US); Nicholas J. Papadopoulos, LaGrangeville, NY (US); George D. Yancopoulos, Yorktown Heights, NY (US); James P. Fandl, LaGrangeville, NY (US); Thomas J. Daly, New City, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 285 days.

This patent is subject to a terminal disclaimer.

(21) Appl. No.: 11/089,803

(22) Filed: Mar. 25, 2005

(65) Prior Publication Data
US 2005/0260203 A1   Nov. 24, 2005

Related U.S. Application Data

(63) Continuation-in-part of application No. 10/988,243, filed on Nov. 12, 2004, which is a continuation-in-part of application No. 10/009,852, filed as application No. PCT/US00/14142 on May 23, 2000, now Pat. No. 7,070,959, which is a continuation-in-part of application No. 10/880,021, filed on Jun. 29, 2004, now Pat. No. 7,279,159, which is a continuation-in-part of application No. 10/609,775, filed on Jun. 30, 2003, now Pat. No. 7,087,411.

(60) Provisional application No. 60/138,133, filed on Jun. 8, 1999.

(51) Int. Cl.
*A61K 38/18* (2006.01)
*C07K 14/71* (2006.01)
*C12N 15/62* (2006.01)

(52) U.S. Cl. .............. 424/134.1; 424/192.1; 514/2; 514/12; 530/350; 536/23.4

(58) Field of Classification Search ............. None
See application file for complete search history.

(56) References Cited

U.S. PATENT DOCUMENTS 6,100,071 A   8/2000   Davis-Smyth

2005/0175610 A1*  8/2005  Wiegand et al. ......... 424/145.1
2006/0030529 A1*  2/2006  Wiegand et al. ............ 514/12
2006/0058234 A1*  3/2006  Daly et al. .................. 514/12
2006/0148705 A1*  7/2006  Daly et al. .................. 514/12
2006/0172944 A1*  8/2006  Wiegand et al. ............ 514/12

FOREIGN PATENT DOCUMENTS

| WO | WO97/44453 | 11/1997 |
| WO | WO98/13071 | 4/1998 |
| WO | WO99/03996 | 1/1999 |

OTHER PUBLICATIONS

Herley et al. (1999). Characterization of the VEGF binding site on the Flt-1 receptor. Biochem Biophys Res Commun. 262(3):731-738.*
Witmer et al. (2003). Vascular endothelial growth factors and angiogenesis in eye disease. Prog. Retin. Eye Res. 22(1):1-29.*
Terman, B.I., et al, "Identification of a new endothelial cell growth factor receptor tyrosine kinase", Oncogene (1991) 6:1677-1683.
Terman, B.I., et al., "Identification of teh KDR tyrosine kinase as a receptor for vascular endothelial cell growth factor", Biochem Biophys Res Comm (1992) 187(3):1579-1586.
Davis-Smyth, T., et al,., 1996, The EMBO Journal 15(18):4919-4927.
Holash, J., et al., (2002) PNAS 99(17):11393-11398.
Heidaran, M.A., et al., (1990) J. Bio. Chem. 265(31):18741-18744.
Cunningham, S.A., et al., (1997) Biochem. Biophys. Res. Comm. 231:596-599.
Fuh, G., et al., (1998) J. Bio. Chem. 273(18):11197-11204.
Wiesmann, C., et al., (1997) Cell 91:695-704.
Barleon, B., et al., (1997) J. Bio. Chem. 272(16):10382-10388.
Davis-Smyth, T., et al., (1998) J. Bio. Chem. 273(6):3216-3222.

* cited by examiner

*Primary Examiner*—Christine J. Saoud
*Assistant Examiner*—Jon M Lockard
(74) *Attorney, Agent, or Firm*—Valeta Gregg, Esq.

(57) ABSTRACT

Modified chimeric polypeptides with improved pharmacokinetics and improved tissue penetration are disclosed useful for treating eye disorders, including age-related macular degeneration and diabetic retinopathy.

11 Claims, 11 Drawing Sheets

| Binding Stoichiometry of hVEGF165 to Flt1D2Flk1D3.FcΔC1(a) & VEGFR1R2-FcΔC1(a) | | |
|---|---|---|
| hVEGF165 (nM) | VEGF/Flt1D2Flk1D3.FcΔC1(a) | VEGF/VEGFR1R2-FcΔC1(a) |
| 1 | 0.93 | 0.98 |
| 10 | 0.97 | 0.94 |
| 50 | 1 | 0.99 |
| Average ± StDev | 0.96 ± 0.03 | 0.97 ± 0.02 |

Fig. 1

SEQUENCE LISTING

<160> NUMBER OF SEQ ID NOS: 23

<210> SEQ ID NO 1
<211> LENGTH: 1453
<212> TYPE: DNA
<213> ORGANISM: homo sapien

<400> SEQUENCE: 1

```
aagcttgggc tgcaggtcga tcgactctag aggatcgatc cccgggcgag ctcgaattcg      60
caaccaccat ggtcagctac tgggacaccg ggtcctgct  gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaaagtttc acttgacac  tttgatccct gatggaaaac     300
gcataatctg gacagtaga  aagggcttca tcatatcaaa tgcaacgtac aaagaaatag     360
ggcttctgac ctgtgaagca acagtcaatg gcatttgta  taagacaaac tatctcacac     420
atcgacaaac caatacaatc atagatgtgg ttctgagtcc gtctcatgga attgaactat     480
ctgttggaga aaagcttgtc ttaaattgta cagcaagaac tgaactaaat gtggggattg     540
acttcaactg gaatacccct tcttcgaagc atcagcataa gaaacttgta aaccgagacc     600
taaaacccca gtctgggagt gagatgaaga attttttgag caccttaact atagatggtg     660
taaccccgga gtgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc cccccaaaac     840
ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
tgatgcatga ggctctgcac aaccactaca cgcagaagag cctctccctg tctccgggta    1440
aatgagcggc cgc                                                       1453
```

<210> SEQ ID NO 2
<211> LENGTH: 458
<212> TYPE: PRT
<213> ORGANISM: homo sapien

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45
```

-continued

```
Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
             100                 105                 110

Thr Asn Tyr Leu Thr His Arg Gln Thr Asn Thr Ile Ile Asp Val Val
         115                 120                 125

Leu Ser Pro Ser His Gly Ile Glu Leu Ser Val Gly Glu Lys Leu Val
     130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 3
<211> LENGTH: 1444
<212> TYPE: DNA
<213> ORGANISM: homo sapien

<400> SEQUENCE: 3

```
aagcttgggc tgcaggtcga tcgactctag aggatcgatc cccgggcgag ctcgaattcg      60
caaccaccat ggtcagctac tgggacaccg ggtcctgct gtgcgcgctg ctcagctgtc     120
tgcttctcac aggatctagt tccggaggta gaccttcgt agagatgtac agtgaaatcc     180
ccgaaattat acacatgact gaaggaaggg agctcgtcat tccctgccgg ttacgtcac     240
ctaacatcac tgttacttta aaaaagtttc cacttgacac tttgatccct gatggaaaac     300
gcataatctg ggacagtaga aagggcttca tcatatcaaa tgcaacgtac aaagaaatag     360
ggcttctgac ctgtgaagca acagtcaatg gcatttgta taagacaaac tatctcacac     420
atcgacaaac caatacaatc atagatatcc agctgttgcc caggaagtcg ctggagctgc     480
tggtagggga aagctggtc ctcaactgca ccgtgtgggc tgagtttaac tcaggtgtca     540
cctttgactg ggactaccca gggaagcagg cagagcgggg taagtgggtg cccgagcgac     600
gctcccaaca gacccacaca gaactctcca gcatcctgac catccacaac gtcagccagc     660
acgacctggg ctcgtatgtg tgcaaggcca caacggcat ccagcgattt cgggagagca     720
ccgaggtcat tgtgcatgaa atggcccgg gcgacaaaac tcacacatgc ccaccgtgcc     780
cagcacctga actcctgggg ggaccgtcag tcttcctctt ccccccaaaa cccaaggaca     840
cccctcatgat ctcccggacc cctgaggtca catgcgtggt ggtggacgtg agccacgaag     900
acccctgaggt caagttcaac tggtacgtgg acggcgtgga ggtgcataat gccaagacaa     960
agccgcggga ggagcagtac aacagcacgt accgtgtggt cagcgtcctc accgtcctgc    1020
accaggactg gctgaatggc aaggagtaca agtgcaaggt ctccaacaaa gccctcccag    1080
cccccatcga gaaaaccatc tccaaagcca agggcagcc ccgagaacca caggtgtaca    1140
ccctgccccc atcccgggat gagctgacca agaaccaggt cagcctgacc tgcctggtca    1200
aaggcttcta tcccagcgac atcgccgtgg agtgggagag caatgggcag ccggagaaca    1260
actacaagac cacgcctccc gtgctggact ccgacggctc cttcttcctc tatagcaagc    1320
tcaccgtgga caagagcagg tggcagcagg ggaacgtctt ctcatgctcc gtgatgcatg    1380
aggctctgca caaccactac acgcagaaga gcctctccct gtctccgggt aaatgagcgg    1440
ccgc                                                                 1444
```

<210> SEQ ID NO 4
<211> LENGTH: 455
<212> TYPE: PRT
<213> ORGANISM: homo sapien

<400> SEQUENCE: 4

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
             20                  25                  30

Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
65                  70                  75                  80
```

```
Trp Asp Ser Arg Lys Gly Phe Ile Ile Ser Asn Ala Thr Tyr Lys Glu
                85                  90                  95
Ile Gly Leu Leu Thr Cys Glu Ala Thr Val Asn Gly His Leu Tyr Lys
            100                 105                 110
Thr Asn Tyr Leu Thr His Arg Gln Thr Asn Thr Ile Ile Asp Ile Gln
        115                 120                 125
Leu Leu Pro Arg Lys Ser Leu Glu Leu Leu Val Gly Glu Lys Leu Val
    130                 135                 140
Leu Asn Cys Thr Val Trp Ala Glu Phe Asn Ser Gly Val Thr Phe Asp
145                 150                 155                 160
Trp Asp Tyr Pro Gly Lys Gln Ala Glu Arg Gly Lys Trp Val Pro Glu
                165                 170                 175
Arg Arg Ser Gln Gln Thr His Thr Glu Leu Ser Ser Ile Leu Thr Ile
            180                 185                 190
His Asn Val Ser Gln His Asp Leu Gly Ser Tyr Val Cys Lys Ala Asn
        195                 200                 205
Asn Gly Ile Gln Arg Phe Arg Glu Ser Thr Glu Val Ile Val His Glu
    210                 215                 220
Asn Gly Pro Gly Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
    450                 455

<210> SEQ ID NO 5
<211> LENGTH: 1377
<212> TYPE: DNA
<213> ORGANISM: homo sapien
```

<400> SEQUENCE: 5

```
atggtcagct actgggacac cggggtcctg ctgtgcgcgc tgctcagctg tctgcttctc     60
acaggatcta gttccggaag tgataccggt agacctttcg tagagatgta cagtgaaatc    120
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaagggcttc atcatatcaa atgcaacgta caagaaaata    300
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata gaaacttgt aaaccgagac     540
ctaaaaaccc agtctgggag tgagatgaag aaattttga gcaccttaac tatagatggt     600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct ccccccaaa acccaaggac     780
accctcatga tctcccggac ccctgaggtc acatgcgtgg tggtggacgt gagccacgaa    840
gaccctgagg tcaagttcaa ctggtacgtg acggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aagggcagc cccgagaacc acaggtgtac    1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 6
<211> LENGTH: 458
<212> TYPE: PRT
<213> ORGANISM: homo sapien

<400> SEQUENCE: 6

```
Met Val Ser Tyr Trp Asp Thr Gly Val Leu Leu Cys Ala Leu Leu Ser
  1               5                  10                  15

Cys Leu Leu Thr Gly Ser Ser Gly Ser Asp Thr Gly Arg Pro
                 20                  25                  30

Phe Val Glu Met Tyr Ser Glu Ile Pro Glu Ile Ile His Met Thr Glu
             35                  40                  45

Gly Arg Glu Leu Val Ile Pro Cys Arg Val Thr Ser Pro Asn Ile Thr
         50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125
```

```
Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 7
<211> LENGTH: 4
<212> TYPE: PRT
<213> ORGANISM: homo sapien

<400> SEQUENCE: 7

Val Val Leu Ser
 1

<210> SEQ ID NO 8
<211> LENGTH: 36
<212> TYPE: DNA
```

```
<213> ORGANISM: Artificial Sequence
<220> FEATURE:
<223> OTHER INFORMATION: Primer

<400> SEQUENCE: 8
gactagcagt ccggaggtag acctttcgta gagatg                               36

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
cggactcaga accacatcta tgattgtatt ggt                                  33

<210> SEQ ID NO 10
<211> LENGTH: 7
<212> TYPE: PRT
<213> ORGANISM: homo sapien

<400> SEQUENCE: 10

Gly Arg Pro Phe Val Glu Met
 1               5

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
acaatcatag atgtggttct gagtccgtct catgg                                35

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
gataatgccc gggccctttt catggaccct gacaaatg                             38

<210> SEQ ID NO 13
<211> LENGTH: 6
<212> TYPE: PRT
<213> ORGANISM: homo sapien

<400> SEQUENCE: 13

Val Arg Val His Glu Lys
 1               5

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gactagcagt ccggaggtag acctttcgta gagatg                               36
```

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
ttcctgggca acagctggat atctatgatt gtattggt                       38

<210> SEQ ID NO 16
<211> LENGTH: 6
<212> TYPE: DNA
<213> ORGANISM: Artificial Sequence
<220> FEATURE:
<223> OTHER INFORMATION: Mutant

<400> SEQUENCE: 16 tccgga                                                           6

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
atccagctgt tgcccaggaa gtcgctggag ctgctggta                      39

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
attttcatgc acaatgacct cggtgctctc ccgaaatcg                      39

<210> SEQ ID NO 19
<211> LENGTH: 38
<212> TYPE: DNA
<213> ORGANISM: Artificial Sequence
<220> FEATURE:
<223> OTHER INFORMATION: Primer

<400> SEQUENCE: 19
tcatagatat ccagctgttg cccaggaagt cgctggag                       38

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
gataatgccc gggccatttt catgcacaat gacctcggt                      39

<210> SEQ ID NO 21
<211> LENGTH: 6
<212> TYPE: PRT
<213> ORGANISM: homo sapien

<400> SEQUENCE: 21

Val Ile Val His Glu Asn
 1               5

<210> SEQ ID NO 22
<211> LENGTH: 720
<212> TYPE: DNA
<213> ORGANISM: homo sapien

<400> SEQUENCE: 22

| | | | | | |
|---|---|---|---|---|---|
| atggtcagct | actgggacac | cggggtcctg | ctgtgcgcgc | tgctcagctg | tctgcttctc | 60 |
| acaggatcta | gttccggaag | tgataccggt | agacctttcg | tagagatgta | cagtgaaatc | 120 |
| cccgaaatta | tacacatgac | tgaaggaagg | gagctcgtca | ttccctgccg | ggttacgtca | 180 |
| cctaacatca | ctgttacttt | aaaaaagttt | ccacttgaca | ctttgatccc | tgatggaaaa | 240 |
| cgcataatct | gggacagtag | aaagggcttc | atcatatcaa | atgcaacgta | caaagaaata | 300 |
| gggcttctga | cctgtgaagc | aacagtcaat | gggcatttgt | ataagacaaa | ctatctcaca | 360 |
| catcgacaaa | ccaatacaat | catagatgtg | ttctgagtc | cgtctcatgg | aattgaacta | 420 |
| tctgttggag | aaaagcttgt | cttaaattgt | acagcaagaa | ctgaactaaa | tgtggggatt | 480 |
| gacttcaact | gggaataccc | ttcttcgaag | catcagcata | agaaacttgt | aaaccgagac | 540 |
| ctaaaaaccc | agtctgggag | tgagatgaag | aaatttttga | gccacttaac | tatagatggt | 600 |
| gtaacccgga | gtgaccaagg | attgtacacc | tgtgcagcat | ccagtgggct | gatgaccaag | 660 |
| aagaacagca | catttgtcag | ggtccatgaa | aaggacaaaa | ctcacacatg | cccaccgtgc | 720 |

<210> SEQ ID NO 23
<211> LENGTH: 240
<212> TYPE: PRT
<213> ORGANISM: homo sapien

<400> SEQUENCE: 23

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

-continued

```
Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240
```

USE OF VEGF INHIBITORS FOR TREATMENT OF EYE DISORDERS

CROSS-REFERENCE TO RELATED APPLICATIONS

This application is a continuation-in-part of application Ser. No. 10/988,243 filed 12 Nov. 2004, which is a continuation-in-part of application Ser. No. 10/009,852 filed 6 Dec. 2001, now U.S. Pat. No. 7,070,959, which is the National Stage of International Application No. PCT/US00/14142 filed 23 May 2000, which claims the benefit under 35 USC § 119(e) of U.S. Provisional 60/138,133 filed 8 Jun. 1999, and this application is a continuation-in-part of application Ser. No. 10/880,021 filed 29 Jun. 2004, now U.S. Pat. No. 7,279,159 which is a continuation-in-part of application Ser. No. 10/609,775 filed 30 Jun. 2003, now U.S. Pat. No. 7,087,411, which applications are herein specifically incorporated by reference in their entireties.

BACKGROUND

Statement Regarding Related Art

A class of cell-derived dimeric mitogens with selectivity for vascular endothelial cells has been identified and designated vascular endothelial cell growth factor (VEGF). VEGF is a dimer with an apparent molecular mass of about 46 kDa with each subunit having an apparent molecular mass of about 23 kDa. The membrane-bound tyrosine kinase receptor, known as Flt (also known as VEGFR2), was shown to be a VEGF receptor (DeVries et al. (1992) Science 255:989-991). Another form of the VEGF receptor, designated KDR or Flk-1 (also known as VEGFR3), is also known to bind VEGF and induce mitogenesis (Terman et al. (1991) Oncogene 6:1677-1683; Terman et al. (1992) Biochem. Biophys. Res. Comm. 187:1579-1586).

U.S. Pat. No. 6,011,003 describes an altered, soluble form of Flt polypeptide capable of binding to VEGF comprising five or fewer complete immunoglobulin domains. WO 97/44453 describes chimeric VEGF receptor proteins comprising amino acid sequences derived from VEGF receptors Flt1 and KDR.

BRIEF SUMMARY OF THE INVENTION

The invention features a therapeutic method for treating or ameliorating an eye disorder, comprising administering a vascular endothelial growth factor (VEGF) inhibitor to a patient in need thereof. In one embodiment, the eye disorder treated is age related macular degeneration. In another embodiment, the eye disorder treated is diabetic retinopathy.

Preferably, the VEGF inhibitor used in the method of the invention comprises an immunoglobulin-like (Ig) domain 2 of a first VEGF receptor and Ig domain 3 of a second VEGF receptor; and a multimerizing component, wherein the first VEGF receptor is Flt1, the second VEGF receptor is Flk1 or Flt4, and the multimerizing component is selected from the group consisting of (i) an amino acid sequence between 1 to about 200 amino acids in length having at least one cysteine residue, and (ii) an immunoglobulin domain, or fragment of an immunoglobulin domain. In specific embodiments, the VEGF inhibitor is a fusion polypeptide "VEGF trap" selected from the group consisting of SEQ ID NO:2 (Flt1D2.Flk1D3FcΔC1(a)), SEQ ID NO:4 (Flt1D2.VEGFR3D3.FCΔC1(a)), SEQ ID NO:6 (VEGFR1R2 FcΔC1(a)), and SEQ ID NO:23. In another embodiment, the VEGF inhibitor is a fusion polypeptide encoded by a nucleotide sequence selected from the group consisting of SEQ ID NO:1, 3, 5, 22, and a nucleotide sequence which, as a result of the degeneracy of the genetic code, differs from the nucleotide sequence of SEQ ID NO:1, 3, 5, and 22.

In a second aspect, the invention features a method for the treatment of a human subject diagnosed with an eye disorder, comprising administering an effective amount of a vascular endothelial growth factor (VEGF) inhibitor to the human subject, the method comprising administering to the subject an initial dose of at least approximately 25-4000 micrograms VEGF inhibitor protein to an affected eye, and administering to the subject a plurality of subsequent doses of the VEGF inhibitor protein in an amount that is approximately the same or less than the initial dose, wherein the subsequent doses are separated in time from each other by at least two weeks. The eye disorder is one of age-related macular degeneration or diabetic retinopathy. In various embodiments, the initial dose is at least approximately 25 to 4000 micrograms of VEGF inhibitor protein. In various embodiments, the subsequent doses are separated in time from each other by at least two weeks to 12 months; more preferably, the subsequent doses are separated in time from each other by at least 3-6 months. The VEGF inhibitor protein is administered directly to the affected eye, including by use of eye drops or intravitreal injection. Preferably, the VEGF inhibitor is a dimer having two fusion polypeptides consisting essentially of an immunoglobulin-like (Ig) domain 2 of Flt1 and Ig domain 3 of Flk1 or Flt4, and a multimerizing component. In specific embodiments, the VEGF inhibitor is a dimer comprising the fusion polypeptide of SEQ ID NO:2, 4, 6, or 23.

Other objects and advantages will become apparent from a review of the ensuing detailed description.

BRIEF DESCRIPTION OF THE FIGURES

FIG. 1. Biacore analysis of binding stoichiometry. Binding stoichiometry was calculated as a molar ratio of bound VEGF165 to the immobilized Flt1D2Flk1D3.FcΔC1(a) or VEGFR1R2-FcΔC1(a), using the conversion factor of 1000 RU equivalent to 1 ng/ml.

DETAILED DESCRIPTION OF THE INVENTION

Figure 2:
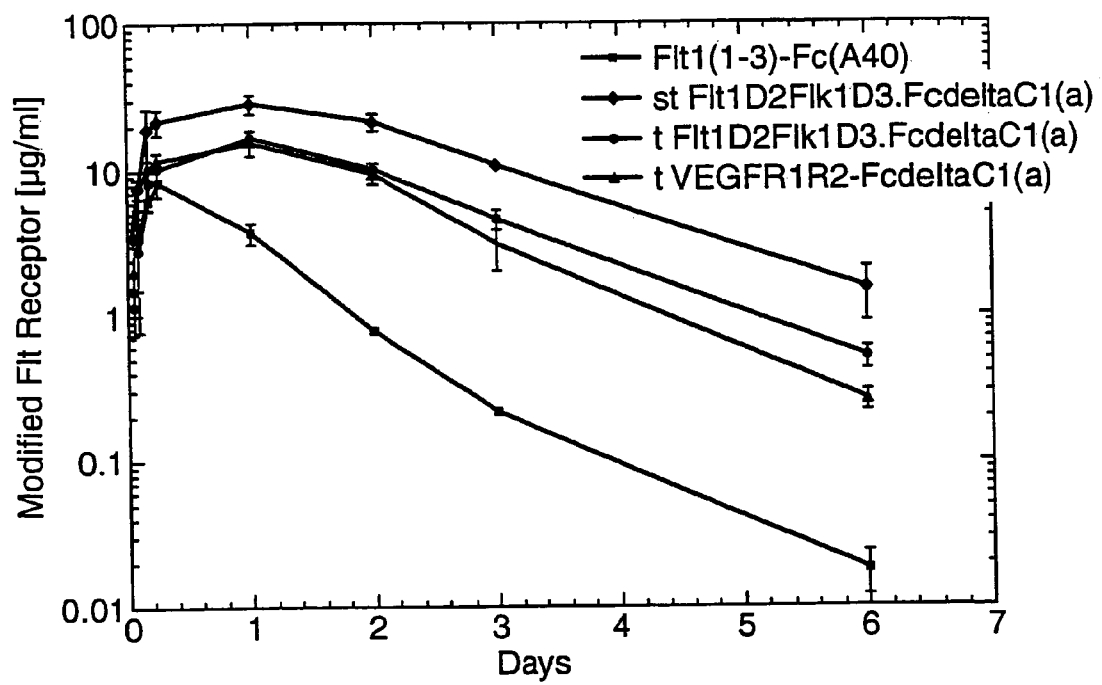
FIG. 2. Pharmacokinetics of Flt1 (1-3)-Fc (A40), Flt1D2.Flk1D3.FcΔC1(a) and VEGFR1R2-FcΔC1(a).

It has been a longstanding problem in the art to produce a receptor-based VEGF antagonist that has a pharmacokinetic profile that is appropriate for consideration of the antagonist as a therapeutic candidate. Applicants describe herein, for the first time, a chimeric polypeptide molecule, capable of antagonizing VEGF activity, that exhibits improved pharmacokinetic properties as compared to other known receptor-based VEGF antagonists. The chimeric polypeptide molecules described herein thus provide appropriate molecules for use in therapies in which antagonism of VEGF is a desired result.

The extracellular ligand binding domain is defined as the portion of a receptor that, in its native conformation in the cell membrane, is oriented extracellularly where it can contact with its cognate ligand. The extracellular ligand binding domain does not include the hydrophobic amino acids associated with the receptor's transmembrane domain or any amino acids associated with the receptor's intracellular domain. Generally, the intracellular or cytoplasmic domain of a receptor is usually composed of positively charged or polar amino acids (i.e., lysine, arginine, histidine, glutamic acid, aspartic acid). The preceding 15-30, predominantly hydrophobic or apolar amino acids (i.e., leucine, valine, isoleucine, and phenylalanine) comprise the transmembrane domain. The extracellular domain comprises the amino acids that precede the hydrophobic transmembrane stretch of amino acids. Usually the transmembrane domain is flanked by positively charged or polar amino acids such as lysine or arginine. von Heijne has published detailed rules that are commonly referred to by skilled artisans when determining which amino acids of a given receptor belong to the extracellular, transmembrane, or intracellular domains (See, von Heijne (1995) BioEssays 17:25).

Nucleic Acid Constructs and Encoded Fusion Polypeptides

The present invention provides for the construction of nucleic acid molecules encoding chimeric polypeptide molecules that are inserted into a vector that is able to express the chimeric polypeptide molecules when introduced into an appropriate host cell. Appropriate host cells include, but are not limited to, bacterial cells, yeast cells, insect cells, and mammalian cells. Any of the methods known to one skilled in the art for the insertion of DNA fragments into a vector may be used to construct expression vectors encoding the chimeric polypeptide molecules under control of transcriptional/translational control signals. These methods may include in vitro recombinant DNA and synthetic techniques and in vivo recombinations (See Sambrook, et al., Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of nucleic acid molecules encoding the chimeric polypeptide molecules may be regulated by a second nucleic acid sequence so that the chimeric polypeptide molecule is expressed in a host transformed with the recombinant DNA molecule. For example, expression of the chimeric polypeptide molecules described herein may be controlled by any promoter/enhancer element known in the art.

Thus, according to the invention, expression vectors capable of being replicated in a bacterial or eukaryotic host comprising chimeric polypeptide molecule-encoding nucleic acids as described herein, are used to transfect the host and thereby direct expression of such nucleic acids to produce the chimeric polypeptide molecules, which may then be recovered in a biologically active form. As used herein, a biologically active form includes a form capable of binding to VEGF. Expression vectors containing the chimeric nucleic acid molecules described herein can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to the inserted chimeric polypeptide molecule sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the chimeric polypeptide molecule DNA sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the chimeric polypeptide molecules.

Cells of the present invention may transiently or, preferably, constitutively and permanently express the chimeric polypeptide molecules.

The chimeric polypeptide molecules may be purified by any technique which allows for the subsequent formation of a stable, biologically active chimeric polypeptide molecule. For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

The method of the invention encompasses the use of a fusion protein consisting essentially of first and second vascular endothelial growth factor (VEGF) receptor components and a multimerizing component, wherein the first VEGF receptor component is an immunoglobulin-like (Ig) domain 2 of Flt1, the second VEGF receptor component is an Ig domain 3 of a Flk1 or Flt4, and the multimerizing component is selected from the group consisting of (i) a multimerizing component comprising a cleavable region (C-region), (ii) a truncated multimerizing component, (iii) an amino acid sequence between 1 to about 200 amino acids in length having at least one cysteine residue, (iv) a leucine zipper, (v) a helix loop motif, (vi) a coil-coil motif, and (vii) an immunoglobulin domain. Examples of the VEGF inhibitors useful in the method of the invention include fusion proteins encoded by a nucleotide sequence selected from the group consisting of the nucleotide sequence of SEQ ID NO:1, 3, 5, 22, and a nucleotide sequence which, as a result of the degeneracy of the genetic code, differs from the nucleotide sequence of SEQ ID NO:1, 3, 5, or 22, and fusion protein selected from the group consisting of SEQ ID NO:2 (Flt1D2.Flk1D3Fc$\Delta$C1(a)), SEQ ID NO:4 (Flt1D2.VEGFR3D3.Fc$\Delta$C1(a)), SEQ ID NO:6 (VEGFR1R2 Fc$\Delta$C1(a)) and (SEQ ID NO:23).

Therapeutic Methods

The present invention also has diagnostic and therapeutic utilities. In particular embodiments of the invention, methods of detecting aberrancies in the function or expression of the chimeric polypeptide molecules described herein may be used in the diagnosis of disorders. In other embodiments, manipulation of the chimeric polypeptide molecules or agonists or antagonists which bind the chimeric polypeptide molecules may be used in the treatment of diseases. In further embodiments, the chimeric polypeptide molecule is utilized as an agent to block the binding of a binding agent to its target.

By way of example, but not limitation, the method of the invention may be useful in treating clinical conditions that are characterized by vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

Combination Therapies

In numerous embodiments, a VEGF inhibitor may be administered in combination with one or more additional compounds or therapies, including a second VEGF inhibitor. Combination therapy includes administration of a single pharmaceutical dosage formulation which contains a VEGF inhibitor molecule and one or more additional agents; as well as administration of a VEGF inhibitor and one or more additional agent(s) in its own separate pharmaceutical dosage formulation. For example, a VEGF inhibitor and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially. The therapeutic methods of the invention may also be combined with other agents or medical procedures used for treatment of eye disorders.

Treatment Population

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is the most common disease affecting the retinal vasculature, and is the leading cause of vision loss among the working age population in the United States. Vascularization of the cornea secondary to injury or disease is yet another category of ocular vascular disease that can lead to severe impairment of vision.

"Macular degeneration" is a medical term that applies to any of several disease syndromes which involve a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type may reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly. It is characterized and usually diagnosed by the presence of elevated levels of two types of cellular debris within the retina, called drusen and lipofuscin.

There are several types of symptomatic treatment, however, that have been used with limited and isolated success, depending on the particular condition of the patient, to treat exudative (wet form) macular degeneration. Laser photocoagulation therapy may benefit certain patients with macular degeneration. However, there are high recurrence rates for selected choroidal neovascular membranes which may initially respond to laser therapy. Vision loss may also result from the laser therapy. Low dose radiation (teletherapy) has also been hypothesized as a possible treatment to induce regression of choroidal neovascularization. Surgical removal of neovascular membranes is another possible treatment, but it is a highly specialized procedure and reportedly has not had promising results to date. There is presently no effective treatment for non-exudative (dry form) macular degeneration. Management of non-exudative macular degeneration is limited to early diagnosis and careful follow-up to determine if the patient develops choroidal neovascularization. Protection against exposure to ultraviolet light and prescribed dosages of anti-oxidant vitamins (e.g., vitamin A, $\beta$-carotene, lutein, zeaxanthin, vitamin C and vitamin E) and zinc may also be of some benefit, but as yet these treatments remain unproven.

Accordingly, the population to be treated by the method of the invention is preferably one of (i) a human subject diagnosed as suffering from macular degeneration, (ii) a human subject diagnosed as suffering from diabetes-related retinopathy, and (iii) a human subject suffering from pathological vascularization of the cornea secondary to injury or disease.

Methods of Administration and Compositions

Preferably, administration of the VEGF inhibitor will be directly to the eye, e.g., topical. Topical methods of administration include, for example, by eye drops, subconjunctival injections or implants, intravitreal injections or implants, sub-Tenon's injections or implants, incorporation in surgical irrigating solutions, etc.

Compositions suitable for topical administration are known to the art (see, for example, U.S. Patent Application 2005/0059639). In various embodiments, compositions of the invention can comprise a liquid comprising an active agent in solution, in suspension, or both. As used herein, liquid compositions include gels. Preferably the liquid composition is aqueous. Alternatively, the composition can take form of an ointment. In a preferred embodiment, the composition is an in situ gellable aqueous composition, more preferably an in situ gellable aqueous solution. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for subconjunctival administration. The microparticles comprising active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent, Upon injection, the polymer forms a depot at the injections site, e.g. by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

In one embodiment of the method of the invention, a human subject with at least one visually impaired eye is treated with 25-4000 micrograms of a VEGF inhibitor protein via intravitreal injection. Improvement of clinical symptoms are monitored by one or more methods known to the art, for example, indirect ophthalmoscopy, fundus photography, fluorescein angiopathy, electroretinography, external eye examination, slit lamp biomicroscopy, applanation tonometry, pachymetry, and autorefaction. Subsequent doses may be administered weekly or monthly, e.g., with a frequency of 2-8 weeks or 1-12 months apart.

Other features of the invention will become apparent in the course of the following descriptions of exemplary embodiments which are given for illustration of the invention and are not intended to be limiting thereof.

EXAMPLES

Example 1

Modified Flt1 Receptor Vector Construction

Chimeric molecules were constructed, denoted R1R2 (Flt1.D2.Flk1D3.FcΔC1(a) and VEGFR1R2-FcΔC1(a) and R1R3 (Flt1D2.VEGFR3D3-FcΔC1(a) and VEGFR1R3-FcΔC1(a) respectively, wherein R1 and Flt1D2=Ig domain 2 of Flt1 (VEGFR1); R2 and Flk1D3=Ig domain 3 of Flk1 (VEGFR2); and R3 and VEGFR3D3=Ig domain 3 of Flt4 (VEGFR3)) were much less sticky to ECM, as judged by an in vitro ECM binding assay and had greatly improved PK as described herein. In addition, these molecules were able to bind VEGF tightly and block phosphorylation of the native Flk1 receptor expressed in endothelial cells.

Construction of the expression plasmid pFlt1D2.Flk1D3.FcΔC1(a). Expression plasmids pMT21.Flt1(1-3).Fc (6519 bp) and pMT21.Flk-1(1-3).Fc (5230 bp) are plasmids that encode ampicillin resistance and Fc-tagged versions of Ig domains 1-3 of human Flt1 and human Flk1, respectively. These plasmids were used to construct a DNA fragment consisting of a fusion of Ig domain 2 of Flt1 with Ig domain 3 of Flk1, using PCR amplification of the respective Ig domains followed by further rounds of PCR to achieve fusion of the two domains into a single fragment. For Ig domain 2 of Flt1, the 5' and 3' amplification primers were as follows: 5': bsp/flt1D2 (5'-GACTAGCAGTCCGGAGGTAGACCTTTCG-TAGAGATG-3') (SEQ ID NO:8), 3': Flt1D2-Flk1D3.as (5'-CGGACTCAGMCCACATCTATGATTGTATTGGT-3') (SEQ ID NO:9). The 5' amplification primer encodes a BspE1 restriction enzyme site upstream of Ig domain 2 of Flt1, defined by the amino acid sequence GRPFVEM (SEQ ID NO:10) corresponding to amino acids 27-33 of SEQ ID NO:2. The 3' primer encodes the reverse complement of the 3' end of Flt1 Ig domain 2 fused directly to the 5' beginning of Flk1 Ig domain 3, with the fusion point defined as TIID of Flt1 (corresponding to amino acids 123-126 of SEQ ID NO:2) and continuing into VVLS (SEQ ID NO:7) (corresponding to amino acids 127-130 of SEQ ID NO:2) of Flk1.

For Ig domain 3 of Flk1, the 5' and 3' amplification primers were as follows: 5': Flt1D2-Flk1D3.s (5'-ACMT-CATAGATGTGGTTCTGAGTCCGTCTCATGG-3') (SEQ ID NO:11); 3': Flk1D3/apa/srf.as (5'-GATAATGC-CCGGGCCCTTTTCATGGACCCTGACAAATG-3') (SEQ ID NO:12). The 5' amplification primer encodes the end of Flt1 Ig domain 2 fused directly to the beginning of Flk1 Ig domain 3, as described above. The 3' amplification primer encodes the end of Flk1 Ig domain 3, defined by the amino acids VRVHEK (SEQ ID NO:13) (corresponding to amino acids 223-228 of SEQ ID NO:2), followed by a bridging sequence that includes a recognition sequence for the restriction enzyme Srf1, and encodes the amino acids GPG. The bridging sequence corresponds to amino acids 229-231 of SEQ ID NO:2.

After a round of PCR amplification to produce the individual domains, the products were combined in a tube and subjected to a further round of PCR with the primers bsp/flt1D2 and Flk1D3/apa/srf.as (described supra) to produce the fusion product. This PCR product was subsequently digested with the restriction enzymes BspEI and SmaI and the resulting 614 bp fragment was subcloned into the BspEI to SrfI restriction sites of the vector pMT21/ΔB2.Fc, to create the plasmid pMT21/Flt1D2.Flk1D3.Fc. The nucleotide sequence of the Flt1D2-Flk1D3 gene fusion insert was verified by standard sequence analysis. This plasmid was then digested with the restriction enzymes EcoRI and SrfI and the resulting 702 bp fragment was transferred into the EcoRI to SrfI restriction sites of the plasmid pFlt1 (1-3)B2-FcΔC1(a) to produce the plasmid pFlt1D2.Flk1D3.FcΔC1(a). The complete DNA and deduced amino acid sequences of the Flt1D2.Flk1D3.FcΔC1(a) chimeric molecule is shown in SEQ ID NO:1-2.

Construction of the expression plasmid pFlt1D2VEGFR3D3FcΔC1(a). The expression plasmid pMT21.Flt1(1-3).Fc (6519 bp) encodes ampicillin resistance and an Fc-tagged version of Ig domains 1-3 of human Flt1 receptor. This plasmid was used to produce a DNA fragment containing Ig domain 2 of Flt1 by PCR. RNA from the cell line HEL921.7 was used to produce Ig domain 3 of Flk1, using standard RT-PCR methodology. A further round of PCR amplification was used to achieve fusion of the two Ig domains into a single fused fragment. For Ig domain 2 of Flt1, the 5' and 3' amplification primers were as follows: 5': bsp/flt1D2 (5'-GACTAGCAGTCCGGAGGTAGAC-CTTTCGTAGAGATG-3') (SEQ ID NO:14), 3': Flt1D2.VEGFR3D3.as (TTCCTGGGCMCAGCTG-GATATCTATGATTGTATTGGT) (SEQ ID NO:15). The 5' amplification primer encodes a BspE1 restriction site upstream of Ig domain 2 of Flt1, defined by the amino acid sequence GRPFVEM (SEQ ID NO:10) (corresponding to amino acids 27-33 of SEQ ID NO:1-2). The 3' amplification primer encodes the reverse complement of the end of Flt1 Ig domain 2 fused directly to the beginning of VEGFR3 Ig domain 3, with the fusion point defined as TIID of Flt1 (corresponding to amino acids 123-126 of SEQ ID NO:4) and continuing into IQLL of VEGFR3 (corresponding to amino acids 127-130 of SEQ ID NO:4).

For Ig domain 3 of VEGFR3, the 5' and 3' primers used for RT-PCR were as follows: 5': R3D3.s (ATCCAGCTGT-TGCCCAGGMGTCGCTGGAGCTGCTGGTA) (SEQ ID NO:17), 3': R3D3.as (ATTTTCATGCACMTGACCTCG-GTGCTCTCCCGAAATCG) (SEQ ID NO:18). Both the 5' and 3' amplification primers match the sequence of VEGFR3. The 296 bp amplification product of this RT-PCR reaction was isolated by standard techniques and subjected to a second round of PCR to add suitable sequences to allow for fusion of the Flt1D2 with the Flk1D3 domains and fusion of the Flk1D3 and Fc domains via a GPG bridge (see below). The amplification primers were as follows: 5':Flt1D2.VEGFR3D3.s(TCATAGATATCCAGCTGTTGC-CCAGGMGTCGCTGGAG) (SEQ ID NO:19), 3': VEGFR3D3/srf.as (GATMTGCCCGGGCCATTTTCATG-CACMTGACCTCGGT) (SEQ ID NO:20). The 5' amplification primer encodes the 3' end of Flt1 Ig domain 2 fused directly to the beginning (5' end) of VEGFR3 Ig domain 3, as described above. The 3' amplification primer encodes the 3' end of VEGFR3 Ig domain 3, defined by the amino acids VIVHEN (SEQ ID NO:21) (corresponding to amino acids 221-226 of SEQ ID NO:4), followed by a bridging sequence that includes a recognition sequence for SrfI, and encodes the amino acids GPG. The bridging sequence corresponds to amino acids 227-229 of SEQ ID NO:4.

After one round (for Flt1 Ig domain 2) or two rounds (for Flt4 Ig domain 3) of PCR to produce the individual Ig domains, the PCR products were combined in a tube and subjected to a further round of PCR amplification with the amplification primers bsp/flt1D2 and VEGFR3D3/srf.as described supra, to produce the fusion product. This PCR product was subsequently digested with the restriction enzymes BspEI and SmaI and the resulting 625 bp fragment was subcloned into the BspEI to SrfI restriction sites of the vector pMT21/Flt1ΔB2.Fc (described supra), to create the plasmid pMT21/Flt1D2.VEGFR3D3.Fc. The sequence of the Flt1D2-VEGFR3D3 gene fusion insert was verified by standard sequence analysis. This plasmid was then digested with the restriction enzymes EcoRI and SrfI and the resulting 693 bp fragment was subcloned into the EcoRI to SrfI restriction sites of the plasmid pFlt1(1-3)ΔB2-FcΔC1(a) to produce the plasmid designated pFlt1D2.VEGFR3D3.FcΔC1(a). The complete DNA deduced amino acid sequence of the Flt1D2.VEGFR3D3.FcΔC1(a) chimeric molecule is shown in SEQ ID NO:3-4.

Example 2

Construction pVEGFR1R2-FcΔC1(a) Expression Vector

The pVEGFR1R2.FcΔC1(a) (SEQ ID NO:15-16) expression plasmid was constructed by insertion of DNA encoding amino acids SDT (corresponding to amino acids 27-29 of SEQ ID NO:6) between Flt1d2-Flk1d3-FcΔC1(a) amino acids 26 and 27 of SEQ ID NO:2 (GG) and removal of DNA encoding amino acids GPG corresponding to amino acids 229-231. The SDT amino acid sequence is native to the Flt1 receptor and was added back in to decrease the likelihood of heterogeneous N-terminal processing. The GPG (bridging sequence) was removed so that the Flt1 and Flk1 Ig domains were fused directly to one another. The complete DNA and deduced amino acid sequences of the pVEGFR1R2.FcΔC1 (a) chimeric molecule is shown in SEQ ID NO:5-6.

Example 3

Cell Culture Process Used to Produce Modified Flt1 Receptors

Cell Culture Process Used to Produce Flt1D2.Flk1D3.FcΔC1(a). The process for production of Flt1D2.Flk1D3.FcΔC1(a) protein using the expression plasmid pFlt1D2.Flk1D3.FcΔC1(a) involves suspension culture of recombinant Chinese hamster ovary (CHO K1/E1A) cells which constitutively express the protein product. The cells are grown in bioreactors and the protein product is isolated and purified by affinity and size exclusion chromatography.

Cell Expansion. Two confluent T-225 $cm^2$ flasks containing the Flt1D2.Flk1D3.FcΔC1(a) expressing cell line were expanded by passaging cells into eight T-225 $cm^2$ flasks in medium (GMEM+10% serum, GIBCO) and incubated at 37° C. and 5% $CO_2$. When the flasks approached confluence (approximately 3 to 4 days) the cells were detached using trypsin. Fresh medium was added to protect the cells from further exposure to the trypsin. The cells were centrifuged and resuspended in fresh medium then transferred to eight 850 $cm^2$ roller bottles and incubated at 37° C. and 5% $CO_2$ until confluent.

Suspension Culture in Bioreactors. Cells grown in roller bottles were trypsinized to detach them from the surface and washed with suspension culture medium. The cells are aseptically transferred to a 5 L bioreactor (New Brunswick Celligen Plus) where the cells are grown in 3.5 L of suspension culture. The suspension culture medium was a glutamine-free low glucose modification of IS-CHO (Irvine Scientific) to which 5% fetal bovine serum (Hyclone), GS supplement (Life Technologies) and 25 μM methionine sulfoximine (Sigma) was added. The pH was controlled at 7.2 by addition of carbon dioxide to the inlet gas or by addition of a liquid solution of sodium carbonate to the bioreactor. Dissolved oxygen level was maintained at 30% of saturation by addition of oxygen or nitrogen to the inlet gas and temperature controlled at 37° C. When a density of $4 \times 10^6$ cells/mL was reached the cells were transferred to a 40 L bioreactor containing the same medium and setpoints for controlling the bioreactor. The temperature setpoint was reduced to 34° C. to slow cell growth and increase the relative rate of protein expression.

Cell Culture Process Used to Produce Flt1D2.VEGFR3D3.FcΔC1(a). The same methodologies as described supra for Flt1D2.Flk1D3.FcΔC1(a) were used to produce Flt1D2.VEGFR3D3.FcΔC1(a).

Example 4

Harvest and Purification of Modified Flt1 Receptors

Harvest and Purification of Flt1D2.Flk1D3.FcΔC1(a). The product protein was aseptically harvested from the bioreactor while retaining cells using Millipore Prostak tangential-flow filtration modules and a low-shear mechanical pump (Fristam). Fresh medium was added to the bioreactor to replace that removed during the harvest filtration. Approximately 40 L of harvest filtrate was then loaded onto a 400 mL column containing Protein A Sepharose resin (Amersham Pharmacia). After loading the resin was washed with buffer containing 10 mM sodium phosphate, 500 mM sodium chloride, pH 7.2 to remove any unbound contaminating proteins. Flt1D2.Flk1D3.FcΔC1(a) protein was eluted with a pH 3.0 citrate buffer. The eluted protein was neutralized by addition of Tris base and frozen at −20° C.

Several frozen lots of Flt1D2.Flk1D3.FcΔC1(a) protein from the Protein A step above were thawed, pooled and concentrated using a Millipore 30 kD nominal molecular weight cutoff (NMWCO) tangential flow filtration membrane. The protein was transferred to a stirred cell concentrator (Millipore) and further concentrated to 30 mg/mL using a 30 kD NMWCO membrane. The concentrated protein was loaded onto a size exclusion column packed with Superdex 200 resin (Amersham Pharmacia) that was equilibrated with phosphate buffered saline plus 5% glycerol. The same buffer was used to run the column. The fractions corresponding to Flt1D2.Flk1D3.FcΔC1(a) dimer were pooled, sterile filtered through a 0.22 micron filter, aliquoted and frozen.

Harvest and Purification of Flt1D2.VEGFR3D3.FcΔC1 (a). The same methodologies as described supra for Flt1D2.Flk1D3.FcΔC1(a) were used to harvest and purify Flt1D2.VEGFR3D3.FcΔC1(a).

Example 5

Binding Stoichiometry of Modified Flt Receptors to VEGF165

Biacore Analysis. The stoichiometry of Flt1D2Flk1D3.FcΔC1(a) and VEGFR1R2-FcΔC1(a) interaction with human VEGF165 was determined by measuring either the level of VEGF saturation binding to the Flt1D2Flk1D3.FcΔC1(a) or VEGFR1R2-FcΔC1(a) surfaces or measuring concentration of VEGF165 needed to completely prevent binding of Flt1D2Flk1D3.FcΔC1(a) or VEGFR1R2-FcΔC1(a) to VEGF Biacore chip surface.

Modified Flt receptors Flt1D2Flk1D3.FcΔC1(a) and VEGFR1R2-FcΔC1(a), were captured with an anti-Fc specific antibody that was first immobilized on a Biacore chip (BIACORE) using amine-coupling chemistry. A blank antibody surface was used as a negative control. VEGF165 was injected at a concentration of 1 nM, 10 nM, and 50 nM over the Flt1D2Flk1D3.FcΔC1(a) and VEGFR1R2-FcΔC1(a) surfaces at 10 µl/min for one hour. A real-time binding signal was recorded and saturation binding was achieved at the end of each injection. Binding stoichiometry was calculated as a molar ratio of bound VEGF165 to the immobilized Flt1D2Flk1D3.FcΔC1(a) or VEGFR1R2-FcΔC1(a), using the conversion factor of 1000 RU equivalent to 1 ng/ml. The results indicated binding stoichiometry of one VEGF165 dimeric molecule per one Flt1D2Flk1D3.FcΔC1(a) or VEGFR1R2-FcΔC1(a) molecule (FIG. 1).

In solution, Flt1D2Flk1D3.FcΔC1(a) or VEGFR1R2-FcΔC1(a) at a concentration of 1 nM (estimated to be 1000 times higher than the KD of the Flt1D2Flk1D3.FcΔC1(a) or VEGFR1R2-FcΔC1(a)/VEGF165 interaction) were mixed with varied concentrations of VEGF165. After one hour incubation, concentrations of the free Flt1D2Flk1D3.FcΔC1 (a) in solution were measured as a binding signal to an amine-coupled VEGF165 surface. A calibration curve was used to convert the Flt1D2Flk1D3.FcΔC1(a) Biacore binding signal to its molar concentration. The data showed that the addition of 1 nM VEGF165 into the Flt1D2Flk1D3.FcΔC1(a) solution completely blocked Flt1D2Flk1D3.FcΔC1(a) binding to the VEGF165 surface. This result suggested the binding stoichiometry of one VEGF165 molecule per one Flt1D2Flk1D3.FcΔC1(a) molecule. When the concentration of Flt1D2Flk1D3.FcΔC1(a) was plotted as a function of added concentration of VEGF165, the slope of the linear portion was −1.06 for Flt1D2Flk1D3.FcΔC1(a) and −1.07 for VEGFR1R2-FcΔC1 (a). The magnitude of the slope, very close to negative one, was indicative that one molecule of VEGF165 bound to one molecule of either Flt1D2Flk1D3.FcΔC1(a) or VEGFR1R2-FcΔC1(a).

Size Exclusion Chromatography. Flt1D2Flk1D3.FcΔC1 (a) was mixed with a 3-fold excess of VEGF165 and the receptor-ligand complex was purified using a Pharmacia Superose 6 size exclusion chromatography column. The receptor-ligand complex was then incubated in a buffer containing 6M guanidine hydrochloride in order to dissociate it into its component proteins. Flt1D2Flk1D3.FcΔC1(a) was separated from VEGF165 using Superose 6 size exclusion chromatography column run in 6M guanidium chloride. In order to determine complex stoichiometry, several injections of Flt1D2Flk1D3.FcΔC1(a) and VEGF165 were made and peak height or peak integrated intensity was plotted as a function of the concentration of injected protein. The calibration was done under conditions identical to those used in separating components of Flt1D2Flk1D3.FcΔC1(a)/VEGF complex. Quantification of the Flt1D2Flk1D3.FcΔC1 (a)/VEGF complex composition was based on the calibration curves. The results of this experiment (FIG. 1) shows the ratio of VEGF165 to Flt1D2Flk1D3.FcΔC1(a) in a complex to be 1:1.

Example 6

Pharmacokinetic Analysis of Modified Flt Receptors

Pharmacokinetic analysis of Flt1(1-3)-Fc (A40), Flt1D2.Flk1D3.FcΔC1(a) and VEGFR1R2-FcΔC1(a). Balb/c mice (25-30 g) were injected subcutaneously with 4 mg/kg of Flt1(1-3)-Fc (A40), CHO transiently expressed Flt1D2.Flk1D3.FcΔC1(a), CHO stably expressed Flt1D2.Flk1D3.FcΔC1(a), and CHO transiently expressed VEGFR1R2-FcΔC1(a). The mice were tail bled at 1, 2, 4, 6, 24 hrs, 2 days, 3 days and 6 days after injection. The sera were assayed in an ELISA designed to detect Flt1(1-3)-Fc (A40), Flt1D2.Flk1D3.FcΔC1(a) or VEGFR1R2-FcΔC1(a). The ELISA involves coating an ELISA plate with VEGF165, binding the detect Flt1(1-3)-Fc (A40), Flt1D2.Flk1D3.FcΔC1(a) or VEGFR1R2-FcΔC1(a) and reporting with an anti-Fc antibody linked to horseradish peroxidase. The results of this experiments are shown in FIG. 2. The $T_{max}$ for Flt1(1-3)-Fc (A40) was at 6 hrs while the $T_{max}$ for the transient and stable Flt1D2.Flk1D3.FcΔC1 (a) and the transient VEGFR1R2-FcΔC1(a) was 24 hrs. The $C_{max}$ for Flt1(1-3)-Fc (A40) was 8 µg/ml. For both transients (Flt1D2.Flk1D3.FcΔC1(a) and VEGFR1R2-FcΔC1(a)) the $C_{max}$ was 18 µg/ml and the $C_{max}$ for the stable VEGFR1R2-FcΔC1(a) was 30 µg/ml.

Figure 3:
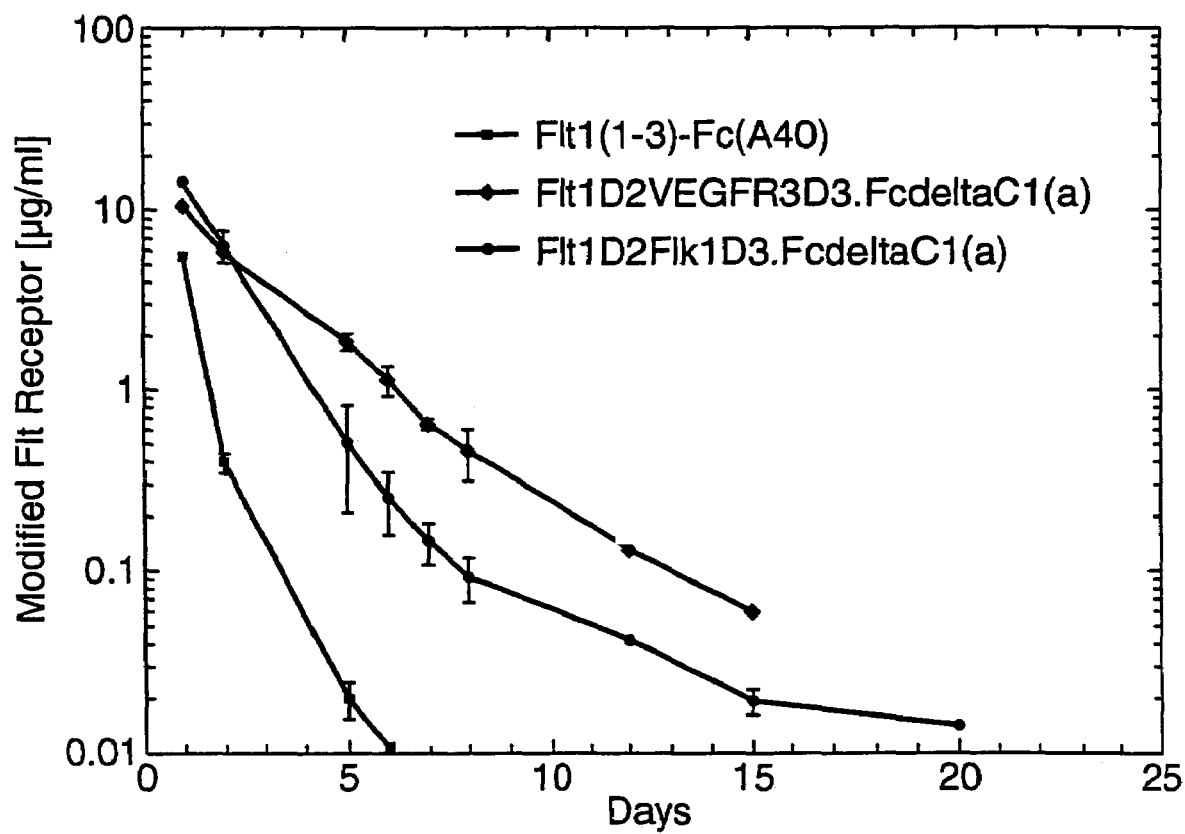
FIG. 3. Pharmacokinetics of Flt1 (1-3)-Fc (A40), Flt1D2.Flk1D3.FcΔC1(a) and Flt1D2.VEGFR3D3.FcΔC1(a).

Pharmacokinetic analysis of Flt1(1-3)-Fc (A40). Flt1D2.Flk1D3.FcΔC1(a) and Flt1D2.VEGFR3D3.FcΔC1(a). Balb/c mice (25-30 g) were injected subcutaneously with 4 mg/kg of Flt1(1-3)-Fc (A40), CHO transiently expressed Flt1D2.Flk1D3.FcΔC1(a) and CHO transiently expressed Flt1D2.VEGFR3D3.FcΔC1(a). The mice were tail bled at 1, 2, 5, 6, 7, 8, 12, 15 and 20 days after injection. The sera were assayed in an ELISA designed to detect Flt1(1-3)-Fc, Flt1D2.Flk1D3.FcΔC1(a) and Flt1D2.VEGFR3D3.FcΔC1(a). The ELISA involves coating an ELISA plate with 165, binding the Flt1(1-3)-Fc, Flt1D2.Flk1D3.FcΔC1(a) or Flt1D2.VEGFR3D3.FcΔC1(a) and reporting with an anti-Fc antibody linked to horseradish peroxidase. Flt1(1-3)-Fc (A40) could no longer be detected in the serum after day 5, whereas Flt1D2.Flk1D3.FcΔC1(a) and Flt1D2.VEGFR3D3.FcΔC1(a) were detectable for 15 days or more. The results of this experiment are shown in FIG. 3.

Example 7

Breakdown of Blood-Retinal Barrier Reversed by Inhibition of VEGF

Rats received a single injection of VEGFR1R2-FcΔC1(a) (SEQ ID NO:6) (25 mg/kg, i.p.) or PBS 4 weeks after induction of diabetes by streptozotocin (65 mg/kg, i.v.). The permeability of retinal vessels was assessed 24 hours later by measuring the extravasation of Evans Blue dye, which binds to albumin in the circulation. Under deep anesthesia, Evans Blue dye (45 mg/kg) was injected intravenously, and allowed to circulate for 60 minutes, and blood samples were taken periodically to assess the concentration of dye in the circulation. The animals were then perfused to flush dye and blood from the vasculature, the eye enucleated and the retinas removed. Evans blue was extracted, and the concentration of dye in the retina was normalized to retinal weight and the time-averaged concentration of Evans blue in the circulation (mL plasma×g retina weight$^{-1}$×hr$^{-1}$) to provide an index of vascular leak. VEGFR1R2-FcΔC1(a) normalized retinal vascular permeability to levels evident in non-diabetic rats.

Example 8

VEGFR1R2-FcΔC1(a) Prevents Neovascularization Induced by Retinal Ischemia

Excessive upregulation of VEGF expression is responsible for pathologic neovascularization in many retinal diseases. The anti-angiogenic properties of VEGFR1R2-FcΔC1(a) were investigated in a mouse model of oxygen-induced ischemic retinopathy (OIR). OIR was produced by transiently exposing mouse pups to increased ambient oxygen (hyperoxia), resulting in obliteration of the developing microvasculature within the central retina. Subsequent return of the animals to room air results in relatively hypoxic conditions in the retina, which in turn stimulates an angiogenic response that shares features with both diabetic retinopathy, retinopathy of prematurity and other ischemic retinopathies. VEGFR1R2-FcΔC1(a) (25 mg/kg, ip) was administered every other day beginning 12-24 hours after returning the mice from hyperoxia to room air. Littermate controls received injections of human Fc following the same schedule. Retinas were collected 1 week following return to room air. Flat mounts were prepared from one retina obtained from each animal, and the retinal vessels stained with fluoresceinated lectin (*Griffonia simplicifolia*). The other retina was embedded and cross-sections were cut and stained with hematoxylin and eosin.

Figure 4:
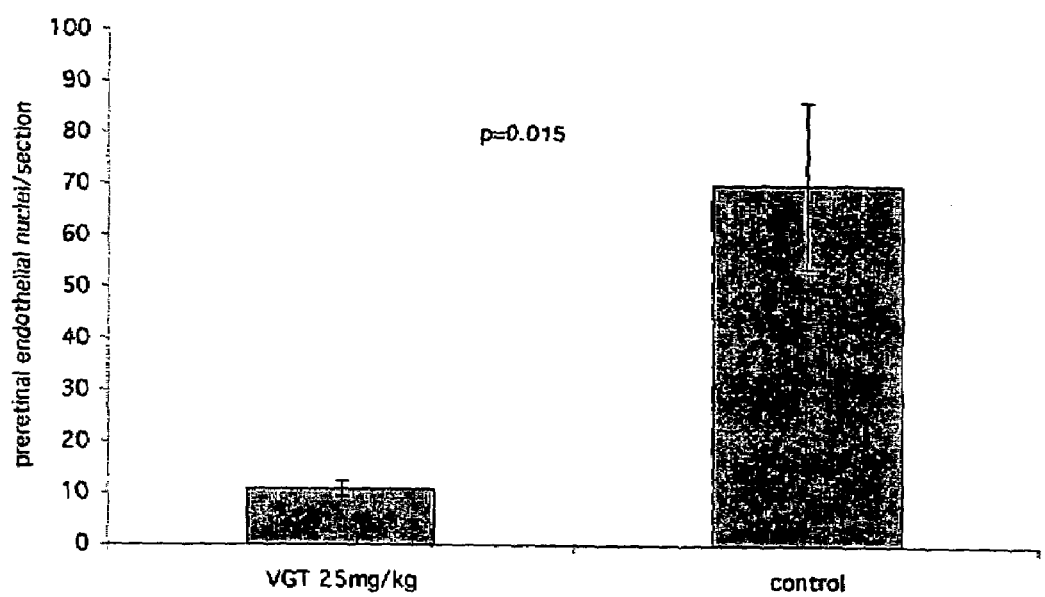
FIG. 4. VEGFR1R2-FcΔC1(a) prevents neovascularization induced by retinal ischemia. Serial 10 μm cross sections were collected and stained with hematoxylin and eosin. For each animal, nuclei in preretinal neovessels were counted in a series of ten sections within 300 microns of the optic nerve head and averaged. Counts were obtained in three independent experiments, n≧4 for each treatment group in each study.

Retinas of all control mice exposed to hyperoxia exhibited marked pathologic angiogenesis, characterized by the presence of vascular tufts penetrating the inner limiting membrane and chaotic sprouting of vessels on the surface of the retina, particularly around the optic nerve head. Administration of VEGFR1R2-FcΔC1(a) almost completely blocked the development of these vascular abnormalities as quantitated by counting endothelial cell nuclei in the abnormal pre-retinal vessels (FIG. 4). Although pathologic angiogenesis was dramatically inhibited, systemic administration of VEGFR1R2-FcΔC1(a) did not block the growth of normal-appearing intraretinal vessels in these animals.

Example 9

Suppression of Choroidal Neovascularization

Figure 5:
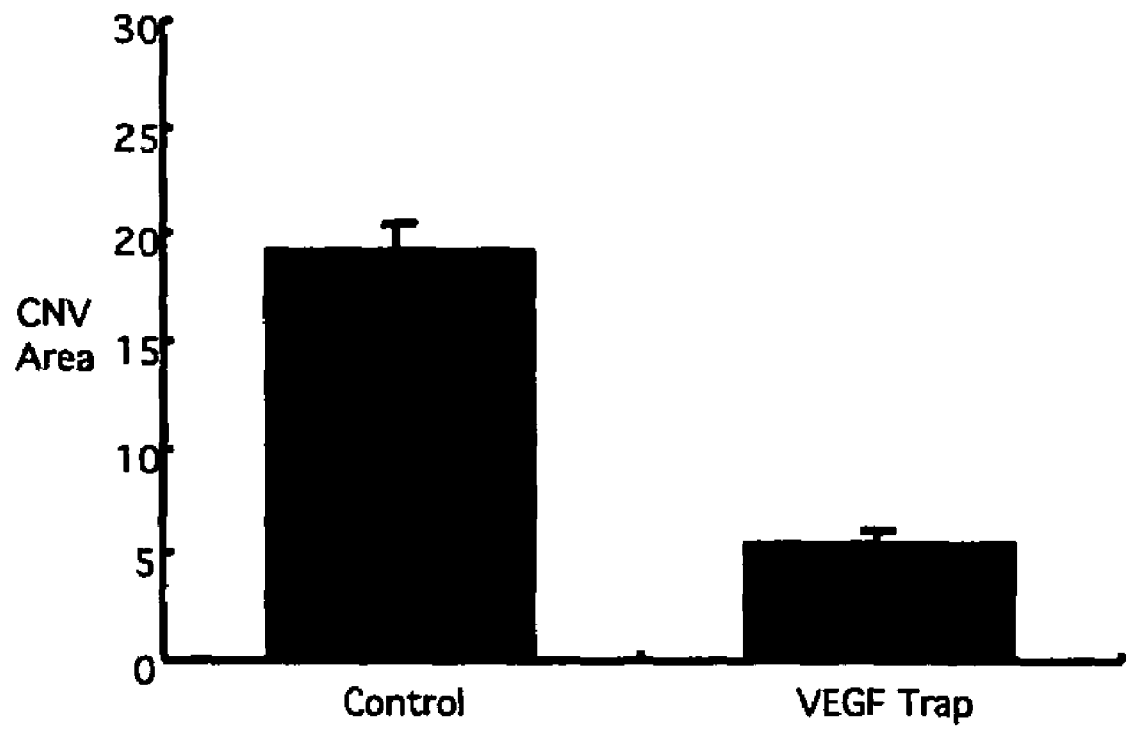
FIG. 5. Effect of subcutaneous VEGFR1R2-FcΔC1(a) injections on choroidal neovascularization area. The size of CNV lesions was measured in choroidal flat mounts. The images were digitized using an Axioskop microscope equipped with a video camera, and the total area of choroidal neovascularization associated with each laser burn was measured using Image-Pro Plus software.

Though animals do not develop age related macular degeneration (AMD) per se, choroidal neovascularization resembling that seen in AMD can be produced by using a laser to produce focal disruptions in Bruch's membrane and the overlying retinal pigment epithelium (RPE). This injury stimulates the abnormal growth of underlying choroidal capillaries into the RPE layer and subretinal space. Disruption of Bruch's membrane is common to all forms of choroidal neovascularization (CNV), including that which characterizes the wet form of AMD. In the laser-induced model of choroidal neovascularization, groups of 9 or 10 mice were treated with subcutaneous (sc) injections of 25 mg/kg of VEGFR1R2-FcΔC1(a) or human Fc one day prior to laser injury and on days 2, 5, 8, and 11 after laser. At 14 days after laser injury, the mice were injected intravenously with fluorescein-labeled dextran (50 mg), euthanized, and eyes were rapidly dissected for choroidal flat mounts or frozen in optimum cutting temperature embedding compound and sectioned for evaluation of the lesions. VEGFR1R2-FcΔC1(a) administration reduced the area of CNV lesions by approximately 70% (FIG. 5).

Figure 9:
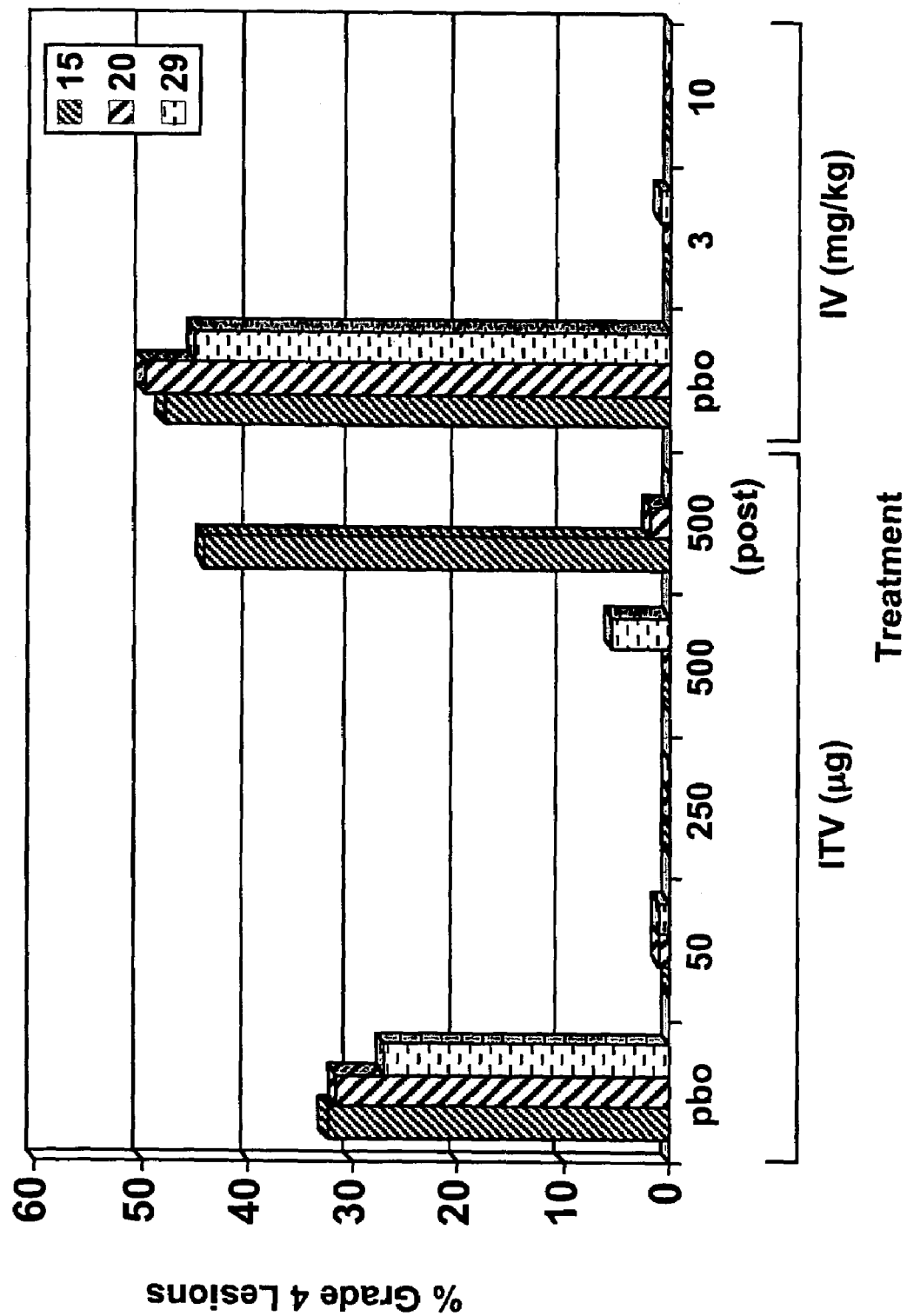
FIG. 9. System or intravitreal VEGF trap protein administration prevents laser-induced choroidal neovascularization (CNV) and reverses vascular leak in established lesions.

The effect of VEGFR1R2-FcΔC1(a) on laser-induced choroidal neovascularization also was evaluated in adult cynomolgus monkeys. In this experiment, VEGFR1R2-FcΔC1(a) was administered by intravenous or intravitreal injection. Each animal received nine or ten laser burns to each retina, and the development of active choroidal neovascular lesions was assessed by fluorescein angiography, once before the initiation of treatment and 15, 20 and 29 days postlaser. VEGFR1R2-FcΔC1(a) was administered intravenously once per week, beginning one week before laser injury, at a dose of 3 mg/kg or 10 mg/kg. Intravitreal injections were made once every two weeks, at a dose of 50, 250 or 500 mcg/eye beginning one week before laser, or once, two weeks following laser (500 mcg dose only), at which time active CNV lesions had already formed. Control animals received weekly intravenous or biweekly intravitreal injections of placebo, beginning one week before laser. Each of the above experimental and control groups comprised six animals, 3 males and 3 females. CNV lesions were visualized by fluorescein angiography and graded. Active CNV lesions characterized bright hyperfluorescence, with late leakage beyond the borders of the laser spot (Grade 4), developed at 32% and 48% of the laser burn sites, in animals receiving intravitreal or intravenous administration of placebo. In contrast, the development of grade 4 lesions was completely or nearly completely prevented in all groups of animals receiving intravenous or intravitreal injections of VEGFR1R2-FcΔC1(a) (FIG. 9). Moreover a single intravitreal injection (500 mcg) of VEGFR1R2-FcΔC1(a) made following the laser injury reduced the incidence of grade 4 lesions from 44% to 0% within 10 days of treatment (FIG. 9).

Example 10

Inhibition of Subretinal Neovascularization in rho/VEGF Transgenic Mice

Figure 6:
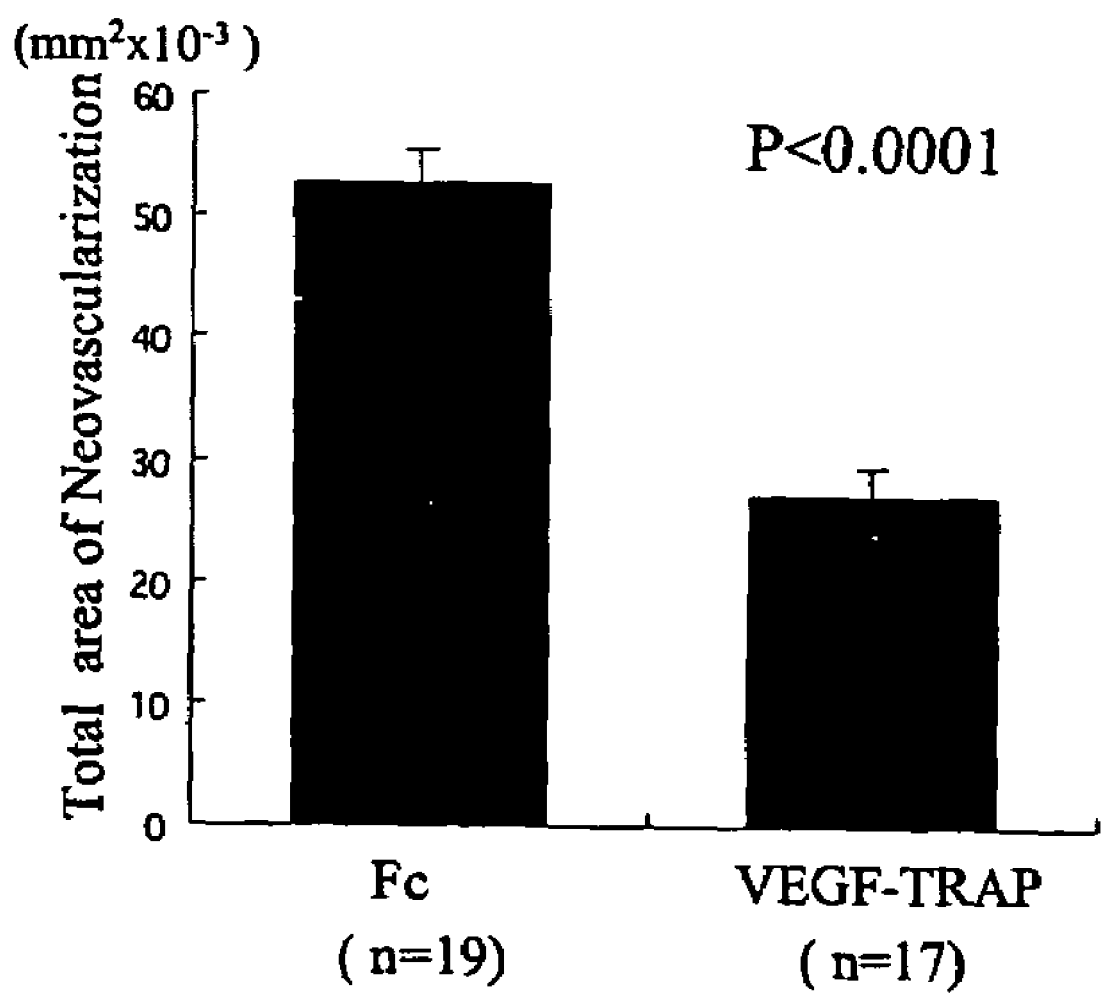
FIG. 6. VEGFR1R2-FcΔC1(a) inhibits subretinal neovascularization in Rho/VEGF transgenic mice.

Transgenic mice expressing a recombinant human VEGF transgene under the control of the rhodopsin promoter (Rho/VEGF) were used in these experiments. These animals begin to express VEGF in photoreceptors on about postnatal day (P) 7, which typically results in pronounced subretinal neovascularization by P21. At P7, mice were divided into 2 groups and treated with 25 mg/kg of VEGFR1R2-FcΔC1(a) (9 mice, 17 eyes) or human Fc (10 mice, 19 eyes) on P7, P10, P13, P16, and P19. On P21, the mice were anesthetized and perfused with fluorescein-labeled dextran. Retinal whole mounts from mice treated with VEGFR1R2-FcΔC1(a) showed few areas of neovascularization while many new vessels were present in the subretinal space of mice that had been treated with Fc. Measurement of the total area of neovascularization per retina by image analysis showed significantly less neovascularization in VEGFR1R2-FcΔC1(a)-treated mice, compared to those treated with Fc (FIG. 6).

Example 11

Suppression of VEGF-Induced Breakdown of the Blood-Retinal Barrier

Figure 7A:
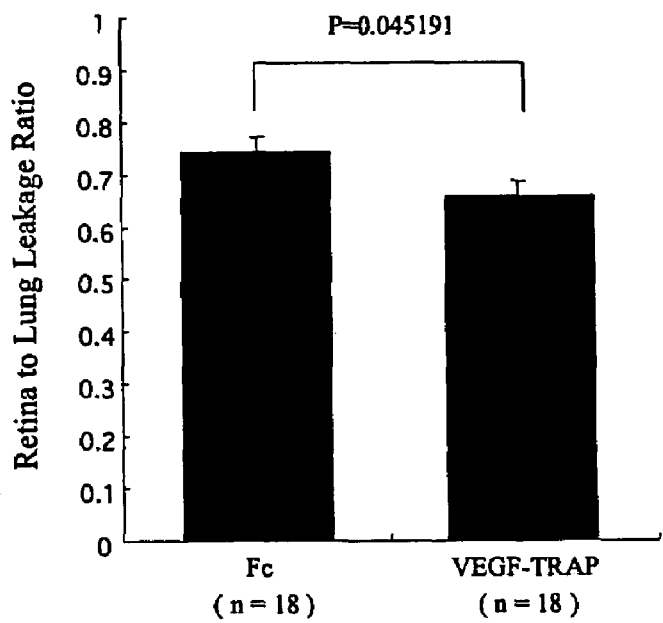
FIG. 7A-B. VEGF-Induced breakdown of the blood retinal barrier. A. Following intravitreal injections of VEGF, adult mice (C57BL/6) treated with injections of VEGFR1R2-FcΔC1(a) had a significantly smaller retina to lung leakage ratio than mice treated with Fc fragment, indicating less breakdown of BRB. B. Double transgenic mice treated with injections of VEGFR1R2-FcΔC1(a) had a significant reduction in the retina to lung leakage ratio compared to mice treated with Fc fragment.

Adult C57BL/6 mice were given a sc injection of 25 mg/kg of VEGFR1R2-FcΔC1(a) or Fc fragment and on the following day received an intravitreous injection of 1 μl of $10^{-6}$ M VEGF. Six hours later, retinal vascular permeability was measured using [$^3$H]-mannitol as a tracer. Mice treated with VEGFR1R2-FcΔC1(a) (9 mice, 18 eyes) had a significantly smaller retina to lung leakage ratio (the ratio of radioactivity in the retina compared to excised lung) than mice treated with Fc fragment (9 mice, 18 eyes) indicating less breakdown of the blood retinal barrier (FIG. 7A).

Figure 7B:
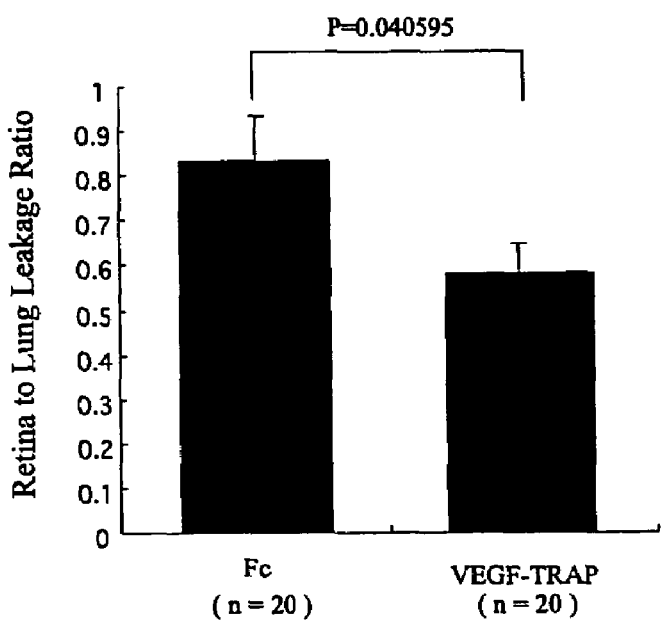

The effect of VEGFR1R2-FcΔC1(a) on VEGF-mediated vascular leak was also evaluated in a second experiment, which employed double transgenic mice (rtTA/rho-TRE/VEGF). These mice are characterized by photoreceptor-specific expression of the VEGF transgene that is inducible by administration of doxycycline. Adult rtTA/rho-TRE/VEGF mice were injected sc with 25 mg/kg VEGFR1R2-FcΔC1(a) (10 mice, 20 eyes) or Fc fragment (10 mice, 20 eyes). On the following day, doxycycline (2 mg/mL) was placed in their drinking water to stimulate over-expression of VEGF within the retina. Two days later, they were given a second sc injection of VEGFR1R2-FcΔC1(a) or Fc fragment and then the next day retinal vascular permeability was measured with [$^3$H]-mannitol. Mice treated with VEGFR1R2-FcΔC1(a) exhibited a significant reduction in the retina to lung leakage ratio compared to mice treated with Fc (FIG. 7B), indicating that impairment in the blood-retinal barrier was ameliorated.

Example 12

Inhibition Injury-Induced Corneal Neovascularization

Corneal neovascularization was induced in male C57Bl/6 mice by intrastromal placement of 3 nylon sutures, or by chemical injury (NaOH) and mechanical debridement of the corneal epithelium. Multiple experiments were conducted in which VEGFR1R2-FcΔC1(a) was administered intraperitoneally once or at multiple time points immediately before or following injury. The growth of corneal neovessels was evaluated by slit-lamp microscopy and histological evaluation. The vasculature was labeled with an endothelial cell specific fluorescein-conjugated lectin, and neovascularization was evaluated in corneal flat-mounts, as well as in cross sections using PECAM immunohistochemistry. The presence of corneal edema was evaluated, using slit lamp microscopy, and corneal thickness was measured in cross-sections; increases in corneal thickness reflect the amount of edema. The numbers of polymorphonuclear leukocytes (PMN) and macrophages were determined by staining cross-sections with HEMA-3 or rat anti-mouse F4/80 monoclonal antibody, respectively.

Figure 8:
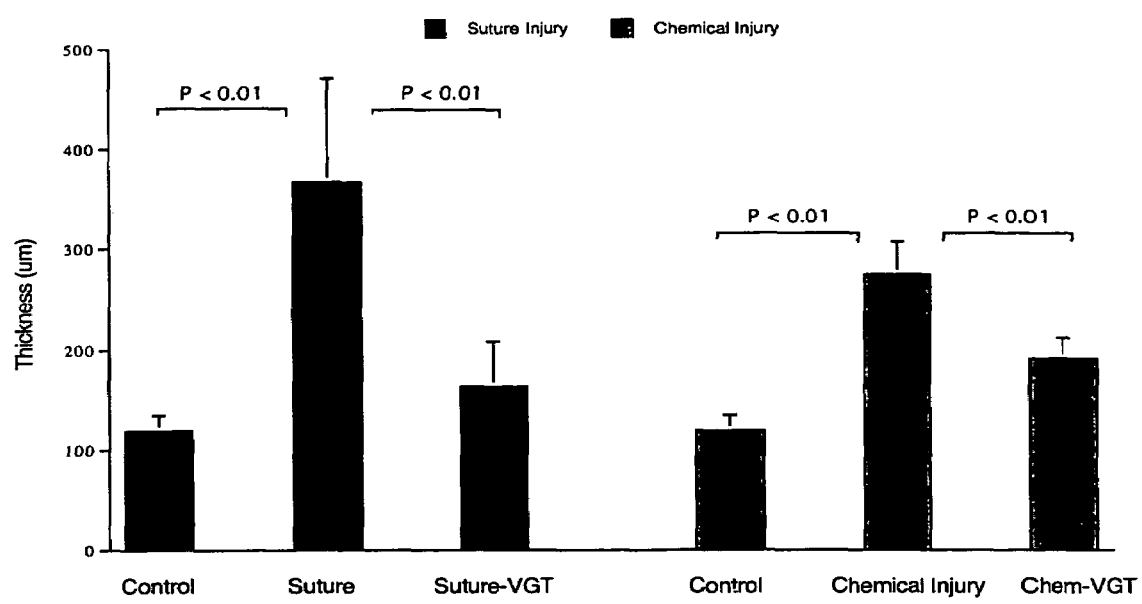
FIG. 8. Effect of VEGFR1R2-FcΔC1(a) administration on corneal thickness in suture and alkali burn models of corneal trauma. Corneas were injured by suture placement or application of NaOH as described, and a single dose of VEGFR1R2-FcΔC1(a) (25 mg/kg, ip) or saline (n=5 per group) was administered immediately following injury. The contralateral cornea served as normal, undamaged controls. Corneas were collected 7 days later and cross-sections were cut and stained with hematoxylin and eosin. Corneal thickness was measured as an index of corneal edema.

Dosing regimens which employed multiple injections of VEGFR1R2-FcΔC1(a) (25 mg/kg, ip) completely inhibited corneal neovascularization in both the suture and chemical injury models. Moreover, single injections of 25 or 12.5 mg/kg VEGFR1R2-FcΔC1(a) given immediately after suture injury effectively blocked corneal neovascularization for at least 9 days, while injections of 6.25 and 2.5 mg/kg ameliorated but did not block corneal neovascularization. The lowest dose of VEGFR1R2-FcΔC1(a) tested (0.5 mg/kg) had no evident effect. Corneal thickness, reflecting the amount of edema present, was significantly reduced in VEGFR1R2-FcΔC1(a)-treated animals compared to vehicle-treated controls (FIG. 8). Histological analyses showed that the infiltration of neutrophils and macrophages into the damaged cornea also was dramatically reduced by VEGFR1R2-FcΔC1(a) treatment.

Example 13

Inhibition of Corneal Neovascularization and Conjunctivalization Following Alkali Burn Injury Corneas were injured by application of NaOH and mechanical debridement of the corneal epithelium in adult, male C57Bl/6 mice. VEGFR1R2-FcΔC1(a) or a control protein (human Fc) was administered subcutaneously (12.5 mg/kg) on days 0 (the day of injury), 7 and 14, at which time reepithelialization of the cornea was complete. The animals were euthanized on days 28 or 42 (14 or 28 days following the last injection of VEGFR1R2-FcΔC1(a) and corneas taken for histological evaluation. Tissues were processed as described above.

Treatment with VEGFR1R2-FcΔC1(a) inhibited corneal neovascularization during the period of active treatment (as determined by slit-lamp microscopy), as well as 2 and 4 weeks following treatment cessation. In eyes evaluated on day 28 (14 days after the last injection of VEGFR1R2-FcΔC1(a), the neovascular response to injury remained completely suppressed and conjunctivalization of the cornea was also inhibited as evidenced by a more normal appearing morphology of the re-epithelialized cornea and a substantial reduction in goblet cell number (~30% relative to controls). Corneal inflammation and edema also were reduced substantially. Evaluation of flat-mounted corneas taken at Day 42 showed that neovascularization was still largely suppressed, though limited, focal sprouting of vessels at the corneal margin was observed in some cases.

The data show that when administered at the time of injury, VEGFR1R2-FcΔC1 (a) improves corneal healing by potently inhibiting the development of corneal neovascularization, inflammation, edema and conjunctivalization of the corneal epithelium. These effects persisted for several weeks following cessation of treatment, suggesting that acute inhibition of VEGF following corneal injury may have long-term benefits.

Example 14

In Vitro Assay with Baf/3 Cells Expressing a Chimeric VEGF Receptor

Materials. Cells: Baf/Flt(1-7)-EpoR, clone C1H. Media: RPMI 1640, 10% fetal bovine serum, penicillin (100 U/ml), streptomycin (100 U/ml) and L-glutamine (2 mM). Growth factor: IL-3 (1 ng/ml). VEGF: VEGF 121 (R&D Biosystems). Detection: WST-8, CCK-8 kit from Dojindo Molecular Technologies. Instruments and analysis: Wallac Victor II Multilabel counter. All data analysed using Graphpad Prizm software with the four parameter logistic equation.

To create a reproducible bioassay having a $K_D$ close to the of the VEGF inhibitor or fusion protein "trap" of SEQ ID NO:6, a chimeric receptor containing the VEGFR1 extracellular domain fused to the cytoplasmic and transmembrane domains of human EpoR via a PGL peptide bridge was constructed. EpoR is able to potently drive proliferation of the mouse pro-B cell line, Baf/3. VEGF binding to the VEGFR1 extracellular domain causing receptor dimerization and activation of EpoR signaling. Neither VEGFR1 nor VEGFR2 native sequence receptors are capable of driving Baf/3 proliferation.

The receptor construct was inserted into a retroviral vector (CMV promotor-chimeric receptor-IRES-GFP) and used to infect Baf/3 cells. Cells expressing GFP (green fluorescent protein) were isolated by 2 rounds of fluorescence activated cell sorting (FACS). This pool was further sorted for expression of VEGFR1. A clonal line was subsequently isolated and used for assay development.

Figure 10:
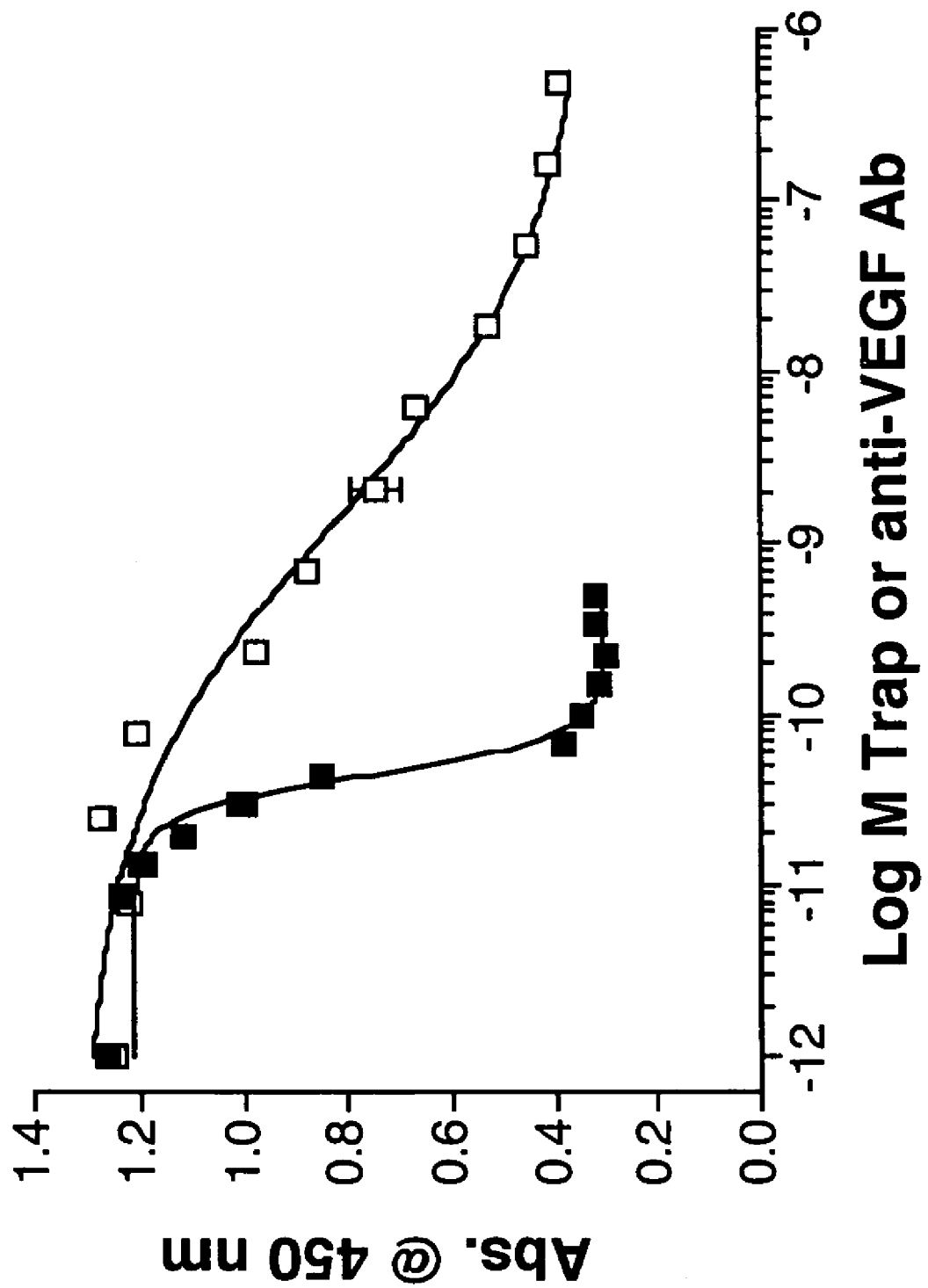
FIG. 10. Dose response curve of Baf/Flt cells grown in VEGF.

The derived cell line proliferates in response to $VEGF_{121}$ with an EC50 of approximately 18 pM after 3 days of growth. The growth response is measured by the bioreduction of the tetrazolium salt WST-8 provided in the CCK-8 kit. The growth response induced by the addition of 70 pM $VEGF_{121}$ is blocked by the VEGF trap protein (SEQ ID NO:6) with an $IC_{50}$ of approximately 40 pM. The $IC_{50}$ in this bioassay is 25 times larger than the biochemically determined Kd of 1.5 pM. FIG. 10 shows the growth response of Baf/Flt cells grown in 0-900 pM VEGF measured by the bioreduction of a tetrazolium salt.

Example 15

Inhibition of VEGF Growth Response by Two Different VEGF Inhibitors

Figure 11:
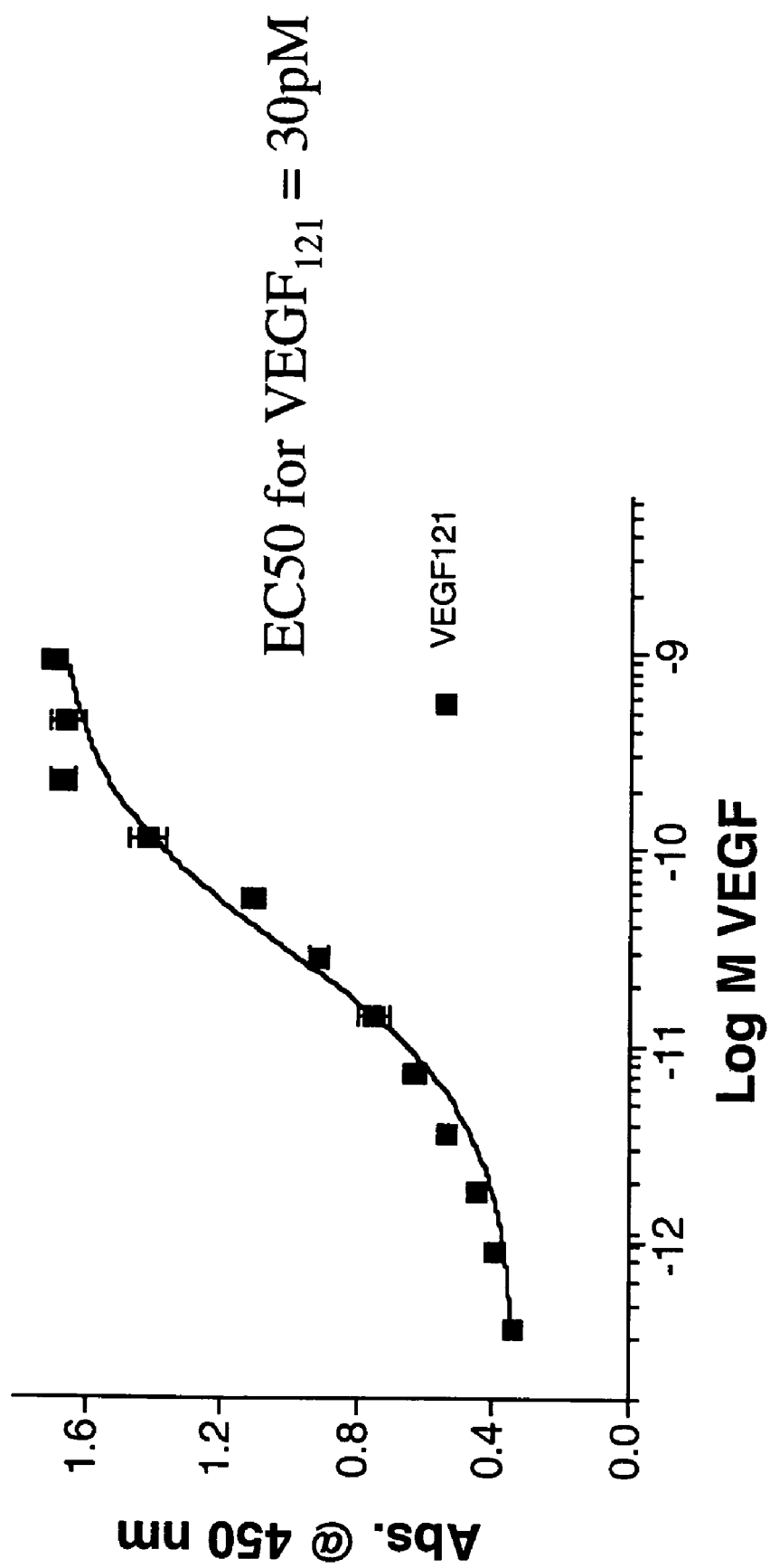
FIG. 11. Inhibition of VEGF growth response by VEGF trap VEGFR1R2-FcΔC1(a) or anti-VEGF antibody.

The in vitro Baf/Flt cell line assay described above was used to measure the effect of two different VEGF inhibitors on the response to VEGF. Cells were incubated for 3 days in 70 pM VEGF and exposed to varying concentrations of VEGF trap (SEQ ID NO:6) (0-500 pM) or an anti-VEGF antibody (Avastin™, Genentech) (0-500 nM). The results are shown in FIG. 11. The $IC_{50}$ for the VEGF trap was 44 pM and for the anti-VEGF antibody 1.4 nM.

Example 16

Pharmacokinetic Analysis of Intravitreal Delivery of Two VEGF Inhibitors

Ocular and systemic levels of two VEGF inhibitors were determined after a single intravitreal administration to male Pigmented New Zealand Cross Bred rabbits. At various time points following the injection, the rabbits were sacrificed and vitreous, retina, and choroid tissues were collected, as well as blood samples for plasma and serum. All samples were analyzed in order to determine tissue and circulating levels of the VEGF trap protein of SEQ ID NO:6 or a truncated version termed a "mini-VEGF trap" lacking the human Fc component (SEQ ID NO:23) (described in U.S. 2004/0014667 and U.S. 2005/0043236, herein incorporated by reference in their entirety), as well as to determine the appropriate pharmacokinetic parameters for the proteins in ocular tissue and plasma. This information allows determination of the ability of an intravitreally administered protein to reach the desired site of action, i.e. the macula in the case of macular degeneration.

Sixty-six male Pigmented New Zealand Cross Bred rabbits (F1 cross New Zealand White and New Zealand Red) were randomly divided into 2 groups with each group consisting of 33 rabbits. The animals in Group 1 were given a single intravitreal injection of full length VEGF trap protein (SEQ ID NO:6) into each eye at a dose of 500 micrograms/eye. The rabbits in Group 2 were given a single intravitreal administration of mini-VEGF trap into each eye at a dose of 250 micrograms/eye. At each time point (predose, 0.25, 1, 6, 24, 72, 168, 336, 504, and 672 hrs postdose), three animals were anesthetized and blood was collected via cardiac puncture in order to obtain plasma and serum. At the time of sacrifice, both eyes were enucleated from each animal and retina, choroids, and vitreous humor were collected.

Sample Processing. Generally, vitreal samples were thawed at room temperature and transferred to individual 5 mL polypropylene tubes. An equivalent weight per volume of RIPA buffer (20 MM Tris HCl, pH 7.5, 5 mM benzamidine, 150 mM sodium chloride, 50 mM sodium fluoride, 1 mM sodium orthovanadate, and 1 mM EDTA) was added to each sample, and homogenized (Cyclone I.Q. Microprocessor, Sentry) for two 45 second cycles at 5,500 rpm. The samples were then incubated for 20 minutes on ice and then centrifuged for 30 minute at 5,500 rpm at 4° C. The supernatant was removed and stored at −80° C. for analysis. Retinal and choroid samples were similarly processed the samples were homogenized for 30-60 seconds at the highest speed setting (Ultra Tunax T8 Homogenizer with S8N-5G Disposing Element, IKA Laboratories). The samples were transferred to individual 1.5 mL eppendorf tubes and incubated for 20 minutes on ice. They were then centrifuged for 30 minutes at 5,500 rpm, 4° C. The supernatant was removed, transferred to a new 1.5 mL eppendorf tube and stored at −80° C. for analysis.

Sample Analysis. In general, VEGF trap protein levels in the samples were measured using an enzyme-linked immunosorbent assay (ELISA) system where micro-titer plates were coated with human $VEGF_{165}$ antigen.

Results. After a single intravitreal injection of the full length or truncated VEGF trap protein into both rabbit eyes, the protein can be detected in both ocular tissue (vitreous humor, retina and choroid) and plasma for up to 672 hrs. These results demonstrated that if a compound is delivered into the vitreous humor, it can be cleared from that region and be distributed into the surrounding tissue, i.e. retina and choroid, before reaching the circulation from which it is eliminated from the body. This is supported not only by the ability to detected and measure the amount of the two traps in the various tissues and plasma, but also by the time it takes for the protein to reach its Cmax in that particular tissue. For mini-VEGF trap protein, it reaches its maximal concentration in the vitreous humor 1 hr after injection. The protein then passes into the retina where the Cmax occurs 6.00 hr after the initial injection. The choroid, which is adjacent to the retina, is with a Tmax of 24.0 hr, after which the protein can reach the circulation and achieve peak levels 72.0 hr after the injections. The full length VEGF trap also displayed a similar tissue progression, although the time frame for reaching the maximal concentrations was longer, in most cases, than that observed for mini-VEGF trap. Peak vitreous humor concentrations of VEGF trap were reached 6 hr after injection; retina followed with a Tmax at 24.0 hr. Choroid tissue had a Tmax of 15 min (0.250 hr), however, this result appears to be driven by a particular sample having an extremely high level of the protein at that time. As observed with the mini-VEGF trap, peak plasma concentrations were reached 72.0 hr after the injections. Since animals injected with mini-VEGF trap received a dose that was half that of the full length protein (250 micrograms/eye vs. 500 micrograms/eye, respectively), the Cmax and AUC values in tissue and plasma tended to be less than that observed for VEGF trap. In the vitreous humor, the Cmax for the mini-VEGF trap was almost half that of the full length protein, 253 micrograms/eye vs. 491 micrograms/mL. In addition, the AUC for the mini-VEGF trap was half that of VEGF trap; there was no apparent difference between the proteins in terms of t1/2 (115 hr vs. 112 hr). In choroid tissue obtained from rabbits which received mini VEGF trap, both the Cmax and AUC values were substantially lower (values were a third (AUC) to an eighth (Cmax) lower) than that observed in samples from VEGF trap treated animals. This difference, especially with regards to AUC, could be accounted for by the decreased elimination t1/2 in the mini VEGF trap samples. The larger protein had a t1/2 of 131 hr while the t1/2 of the smaller protein was 70.9 hr. This same scenario was observed with regards to the plasma samples. The full length VEGF trap samples had a greater Cmax, AUC and t1/2 than samples obtained from the smaller protein. In contrast to these other tissues, in retinal homogenates, both VEGF trap and mini VEGF trap had similar pharmacokinetic profiles. Despite receiving significantly different intravitreal doses, retinal homogenates had Cmax and AUC measurements that were nearly identical. The elimination half-life was shorter, however, in retinal tissue obtained from mini1VEGF trap injected rabbits (132 hr vs. 114 hr).

The results of this study demonstrate that both full-length VEGF trap and mini-VEGF trap can be injected intravitreally and that the proteins penetrate to the desired site of action, i.e. retina or related structure. The results show that the protein is present in the eye tissue for up to 672 hrs, thus allowing for monthly treatment paradigms. Further, once the mini-VEGF trap moves out of the eye tissue into the systemic circulation, it is cleared more quickly from the body than the full-length VEGF trap, thus reducing unwanted systemic action.

Example 17

Treatment of Age-Related Macular Degeneration

A patient manifesting age-related macular degeneration is treated with an intravitreal injection of the VEGF trap protein of SEQ ID NO:6 or 23. The purpose of this treatment is to reduce or prevent the development of neovascularization, macular disease, and retinal damage. Once a patient reaches the age of 60, increased ophthalmic surveillance is performed to detect the presence of AMD. This increased surveillance should include periodic retinal examinations and fluorescein angiograms to monitor for the presence of subretinal fluid, blood, exudates, RPE detachment, cystic retinal changes, or the presence of grayish green subretinal neovascular membrane. When AMD is diagnosed, a regime of VEGF trap protein treatment is commenced coupled with or without other treatments such as photocoagulation. As the first step of treatment, the patient is to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, electroretinography and A-scan measurements. Following the preliminary examination, an intravitreal injection of VEGF trap protein is given to the patient's affected eye manifesting AMD. If both eyes are affected, they may be treated separately. The eye to be treated is injected with 25-4000 micorgrams of VEGF trap protein in an ophthalmic solution.

After treatment, the patients' eyes are to be examined on days one (1), two (2), seven (7), fifteen (15), thirty (30) and sixty (60). Because of the possibility of reoccurrence, the patient should return for periodic examinations on a monthly basis thereafter. On each examination day the patient is monitored for vitreous liquefaction. Additionally, the patient is monitored for posterior vitreous detachments using indirect ophthalmoscopy with scleral depression. Finally, the extent of AMD presented by the patient is continuously monitored through periodic retinal examinations and fluorescein angiograms to monitor for the presence of subretinal fluid, blood, exudates, RPE detachment, cystic retinal changes, or the presence of grayish green subretinal neovascular membrane. Additional VEGF trap protein treatments may be required if indicia of reoccurring neovascularization are observed. Additional treatments may be given on weekly or monthly basis. In a preferred embodiment, an initial treatment is followed by subsequent treatments between 1-6 months apart.

We claim:

1. A therapeutic method for treating or ameliorating an eye disorder, comprising administering a fusion polypeptide capable of binding vascular endothelial growth factor (VEGF) to a patient in need thereof, wherein the fusion polypeptide consists of an immunoglobulin-like (Ig) domain 2 of a first VEGF receptor Flt1 and Ig domain 3 of a second VEGF receptor Flk1 or Flt4; and a multimerizing component, wherein the multimerizing component is an immunoglobulin domain or fragment of an immunoglobulin domain, wherein the eye disorder is selected from the group consisting of age related macular degeneration and diabetic retinopathy, and wherein administration is selected from the group consisting of eye drops, subconjunctival injection, subconjunctival implant, intravitreal injection, intravitreal implant, sub-Tenon's injection, and sub-Tenon's implant.

2. The therapeutic method of claim 1, wherein the fusion polypeptide comprises SEQ ID NO:6.

3. A therapeutic method for treating or ameliorating an eye disorder, comprising administering a dimeric protein comprising two fusion polypeptides, wherein each fusion polypeptide consists of the amino acid sequence of SEQ ID NO:6, wherein the eye disorder is selected from the group consisting of age related macular degeneration and diabetic retinopathy, and wherein administration is selected from the group consisting of eye drops, subconjunctival injection, subconjunctival implant, intravitreal injection, intravitreal implant, sub-Tenon's injection, and sub-Tenon's implant.

4. A method for the treatment of a human subject diagnosed with age-related macular degeneration, comprising administering an effective amount of a vascular endothelial growth factor (VEGF) inhibitor to the human subject, the method comprising:
  (a) administering to the subject an initial dose of at least approximately 25-4000 micrograms VEGF inhibitor protein per eye; and
  (b) administering to the subject a plurality of subsequent doses of the VEGF inhibitor protein in an amount that is approximately the same or less than the initial dose, wherein the subsequent doses are separated in time from each other by at least two weeks, wherein the VEGF inhibitor is a dimeric protein comprising two fusion polypeptides, wherein each fusion polypeptide consists of an immunoglobulin-like (Ig) domain 2 of a first VEGF receptor Flt1 and Ig domain 3 of a second VEGF receptor Flk1 or Flt4, and a multimerizing component, and wherein the multimerizing component is an immunoglobulin domain or fragment of an immunoglobulin domain, and wherein administration is selected from the group consiting of eye drops, subconjunctival injection, subconjunctival implant, intravitreal injection, intravitreal implant, sub-Tenon's injection, and sub-Tenon's implant.

5. The method of claim 4, wherein the initial dose is at least approximately 50 micrograms of VEGF inhibitor protein.

6. The method of claim 5, wherein the initial dose is at least approximately 100 micrograms of VEGF inhibitor protein.

7. The method of claim 6, wherein the initial dose is at least approximately 1000 micrograms of VEGF inhibitor protein.

8. The method of claim 4, wherein the subsequent doses are separated in time from each other by at least four weeks.

9. The method of claim 8, wherein the subsequent doses are separated in time from each other by at least 3 to 6 months.

10. The method of claim 4, wherein the initial dose and at least one subsequent dose is administered by intravitreal injection.

11. The method of claim 4, wherein the VEGF inhibitor is a dimer having two fusion polypeptides, wherein each fusion polypeptide comprises the amino acid sequence of SEQ ID NO:6.

* * * * *